US008900207B2

(12) United States Patent
Uretsky

(10) Patent No.: US 8,900,207 B2
(45) Date of Patent: Dec. 2, 2014

(54) APPARATUS AND METHOD FOR TREATMENT OF BIFURCATION LESIONS

(76) Inventor: Barry F. Uretsky, Fort Smith, AR (US)

(*) Notice: Subject to any disclaimer, the term of this patent is extended or adjusted under 35 U.S.C. 154(b) by 986 days.

(21) Appl. No.: 12/201,871

(22) Filed: Aug. 29, 2008

(65) Prior Publication Data

US 2010/0057020 A1 Mar. 4, 2010

(51) Int. Cl.
*A61M 25/00* (2006.01)
*A61F 2/954* (2013.01)
*A61F 2/958* (2013.01)
*A61F 2/86* (2013.01)
*A61F 2/06* (2013.01)
*A61M 25/01* (2006.01)
*A61M 25/10* (2013.01)

(52) U.S. Cl.
CPC .......... *A61M 25/0029* (2013.01); *A61F 2/954* (2013.01); *A61F 2/958* (2013.01); *A61F 2/86* (2013.01); *A61F 2002/065* (2013.01); *A61M 25/0105* (2013.01); *A61M 25/1002* (2013.01); *A61M 25/104* (2013.01); *A61M 2025/004* (2013.01); *A61M 2025/0183* (2013.01)
USPC .......................... 604/284; 604/533; 623/1.35

(58) Field of Classification Search
USPC .............. 623/1.11, 1.12, 1.23, 1.35; 606/108, 606/191–194; 604/507–510, 264, 523, 533, 604/538
See application file for complete search history.

(56) References Cited

U.S. PATENT DOCUMENTS

| | | | |
|---|---|---|---|
| 4,994,071 A | 2/1991 | MacGregor | |
| 5,295,969 A | 3/1994 | Fischell et al. | |
| 5,613,980 A | 3/1997 | Chauhan | |
| 5,632,772 A | 5/1997 | Alcime et al. | |
| 5,669,924 A | 9/1997 | Shaknovich | |
| 5,697,380 A | 12/1997 | Quiachon et al. | |
| 5,720,735 A | 2/1998 | Dorros | |
| 5,938,623 A | 8/1999 | Quiachon et al. | |
| 6,039,743 A | 3/2000 | Quiachon et al. | |
| 6,086,611 A | 7/2000 | Duffy et al. | |
| 6,117,117 A | 9/2000 | Mauch | |
| 6,129,738 A | 10/2000 | Lashinski et al. | |
| 6,142,973 A | 11/2000 | Carleton et al. | |
| 6,165,195 A | 12/2000 | Wilson et al. | |

(Continued)

OTHER PUBLICATIONS

Yves Louvard et al., "Classification of Coronary Artery Bifurcation Lesions and Treatments," Catheterization and Cardiovascular Interventions, 71:175-183 (2008), Wiley-Liss.

(Continued)

*Primary Examiner* — Thomas J Sweet
*Assistant Examiner* — Matthew Schall
(74) *Attorney, Agent, or Firm* — Mark Murphey Henry

(57) ABSTRACT

Each arterial bifurcation lesion has a fingerprint-like pattern related to varying amounts of plaque and degree of obstruction in the main vessel proximal to, within the bifurcation itself, and the distal limbs of the main branch and side branch (es) and related to the angle of the bifurcation. A new device and with it a new technique is described to optimize treatment of bifurcation (and trifurcation) lesions. The invention and related method use a catheter capable of delivering two or more guide wires exiting at the distal end of the catheter allowing treatment of lesions more safely and efficaciously. Safety is increased by allowing both guide wires to remain in place throughout the entire procedure. Efficacy is increased, particularly in the long-term, by providing a result that maximizes vessel coverage and normal flow dynamics in the entire bifurcation area. Contemplated is the use not only of multiple guide wires but also modified balloon with a tapered design to optimize flow dynamics at the bifurcation in the final result.

4 Claims, 27 Drawing Sheets

(56) References Cited

U.S. PATENT DOCUMENTS

| | | |
|---|---|---|
| 6,210,380 B1 | 4/2001 | Mauch |
| 6,221,080 B1 | 4/2001 | Power |
| 6,221,090 B1 | 4/2001 | Wilson |
| 6,221,098 B1 | 4/2001 | Wilson et al. |
| 6,258,073 B1 | 7/2001 | Mauch |
| 6,258,115 B1 | 7/2001 | Dubrul |
| 6,264,682 B1 | 7/2001 | Wilson et al. |
| 6,361,544 B1 | 3/2002 | Wilson et al. |
| 6,361,555 B1 | 3/2002 | Wilson |
| 6,383,213 B2 | 5/2002 | Wilson et al. |
| 6,387,120 B2 | 5/2002 | Wilson et al. |
| 6,428,567 B2 | 8/2002 | Wilson et al. |
| 6,471,656 B1 | 10/2002 | Shalman et al. |
| 6,475,208 B2 | 11/2002 | Mauch |
| 6,482,211 B1 | 11/2002 | Choi |
| 6,494,875 B1 | 12/2002 | Mauch et al. |
| 6,508,836 B2 | 1/2003 | Wilson et al. |
| 6,520,987 B1 | 2/2003 | Plante |
| 6,579,312 B2 | 6/2003 | Wilson et al. |
| 6,582,394 B1 | 6/2003 | Reiss et al. |
| 6,599,315 B2 | 7/2003 | Wilson |
| 6,709,440 B2 | 3/2004 | Callol et al. |
| 6,749,628 B1 | 6/2004 | Callol et al. |
| 6,780,174 B2 | 8/2004 | Mauch |
| 6,875,227 B2 | 4/2005 | Yoon et al. |
| 6,896,694 B1 | 5/2005 | Filho et al. |
| 6,896,699 B2 | 5/2005 | Wilson et al. |
| 6,926,692 B2 | 8/2005 | Katoh et al. |
| 6,939,368 B2 | 9/2005 | Simso |
| 6,955,688 B2 | 10/2005 | Wilson et al. |
| 7,220,275 B2 | 5/2007 | Davidson et al. |
| 7,341,598 B2 | 3/2008 | Davidson et al. |
| 7,344,514 B2 | 3/2008 | Shanley |

OTHER PUBLICATIONS

Antonio Colombo et al., "Drug-Eluting Stent Update 2007," Circulation, 116:1424-1432 (2007), American Heart Ass'n, Dallas, TX.

Yoshinobu Murasato et al., "Three-Demnsional Modeling of Double-Stent Techniques at the Left Main Coronary Atery Bifurcation Using Micro-Focus X-Ray Computed Tomography," Catheterization and Cardiovascular Interventions, 70:211-220 (2007), Wiley-Liss, Inc.

Alessandro Alberti et al., "'Skirt' Technique for Coronary Artery Bifurcation Stenting," Journal of Invasive Cardiology, 12(12):633-636 (Dec. 2000), HMP Comm'n, Malvern, PA.

Azeem Latib et al., "Bifurcation Disease: What Do We Know, What Should We Do?" Cardiovascular Interventions, 1(3):218-226 (2008), Elsevier Inc.

Yoshinobu Murasato et al., "The Skirt Technique: A Stenting Technique to Treat a Lesion Immediately Proximal to the Bifurcation (Pseudobifurcation)," Catheterization and Cardiovascular Interventions, 51:347-351 (2000), Wiley-Liss, Inc.

David Rizik et al., "Bifurcation Coronary Artery Disease: Current Techniques and Future Directions (Part 2)," Journal of Invasive Cardiology, 20(3):135-141 (2008).

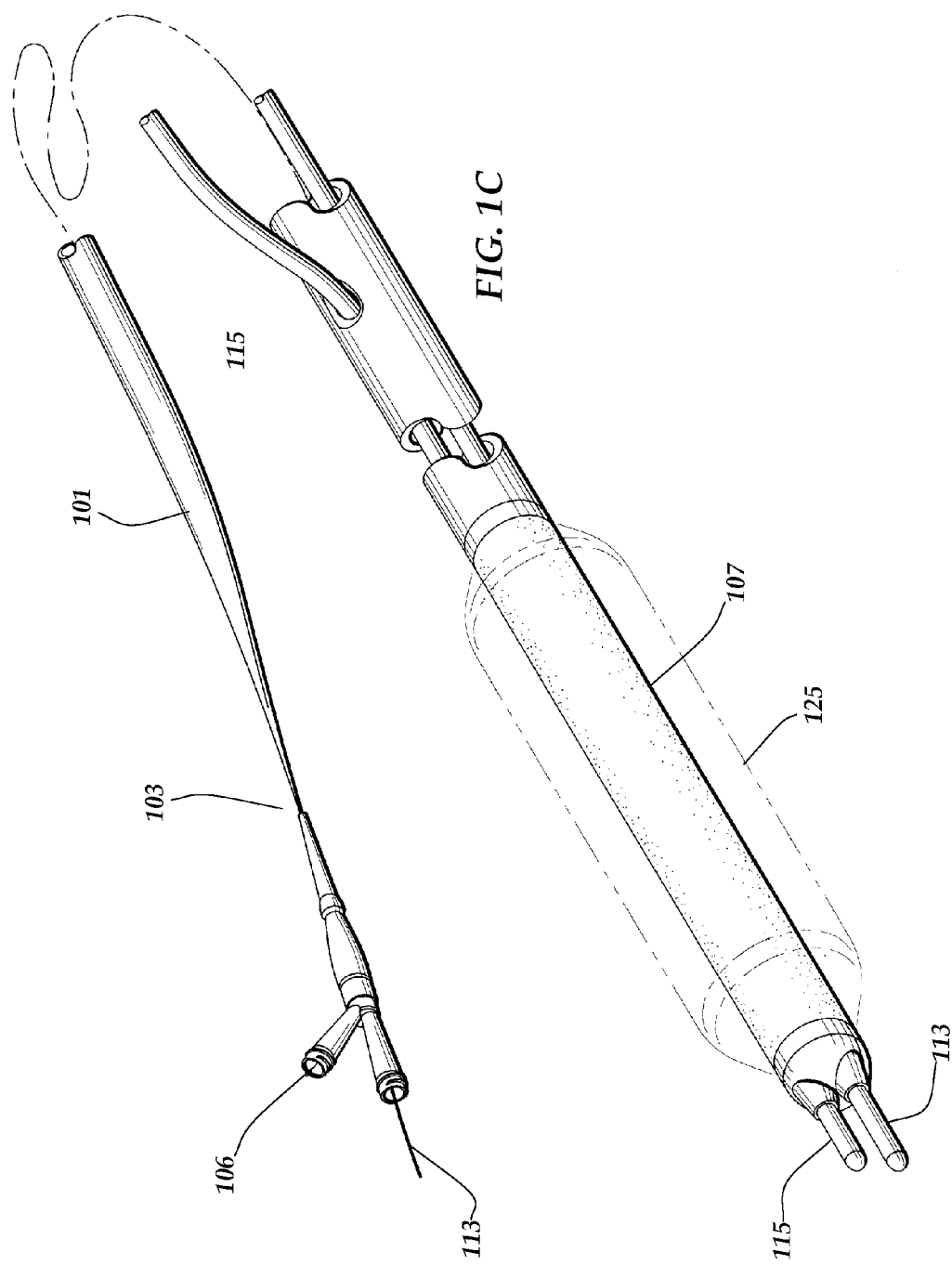

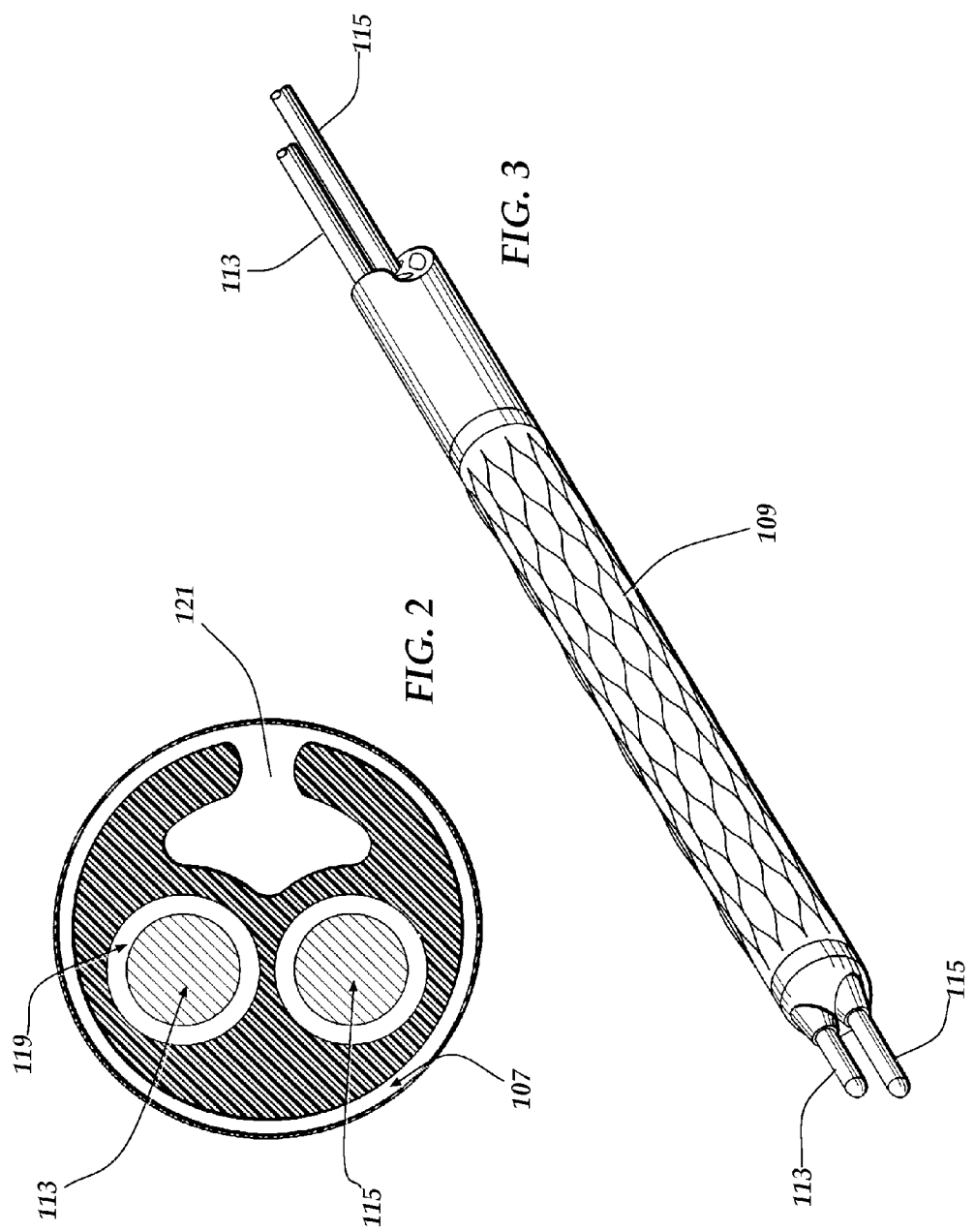

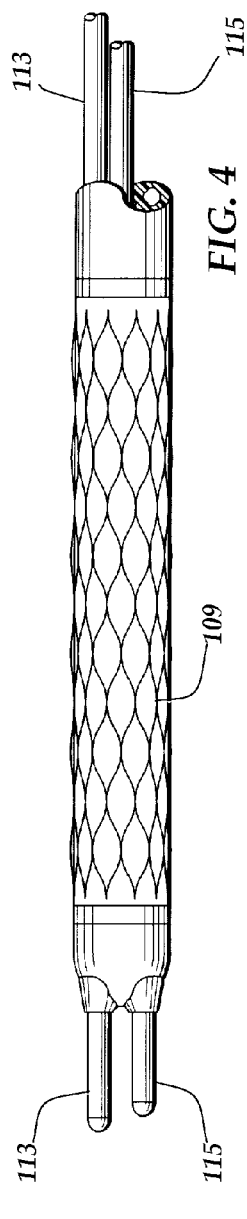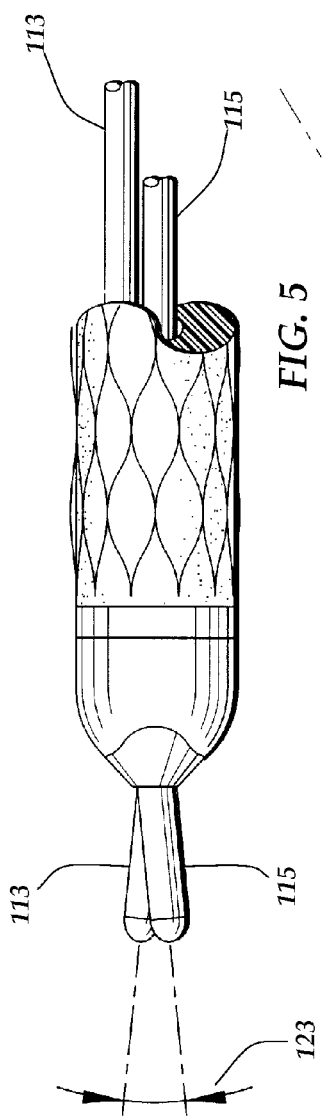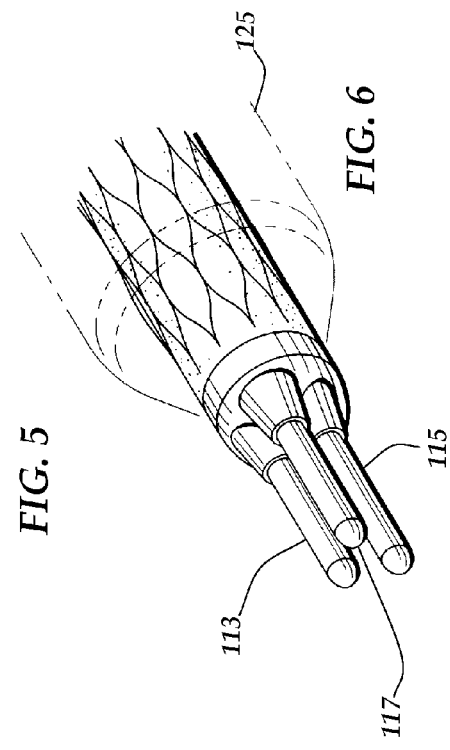

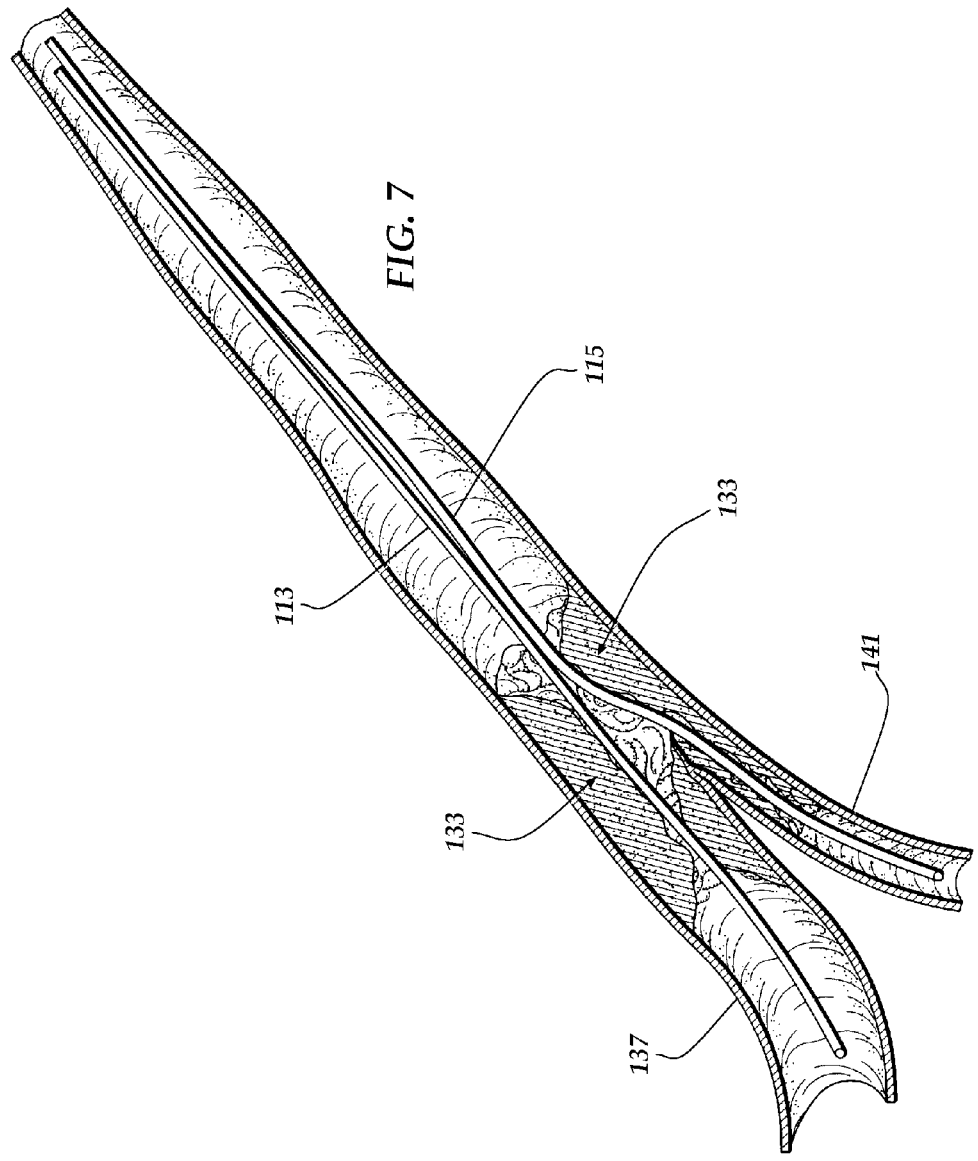

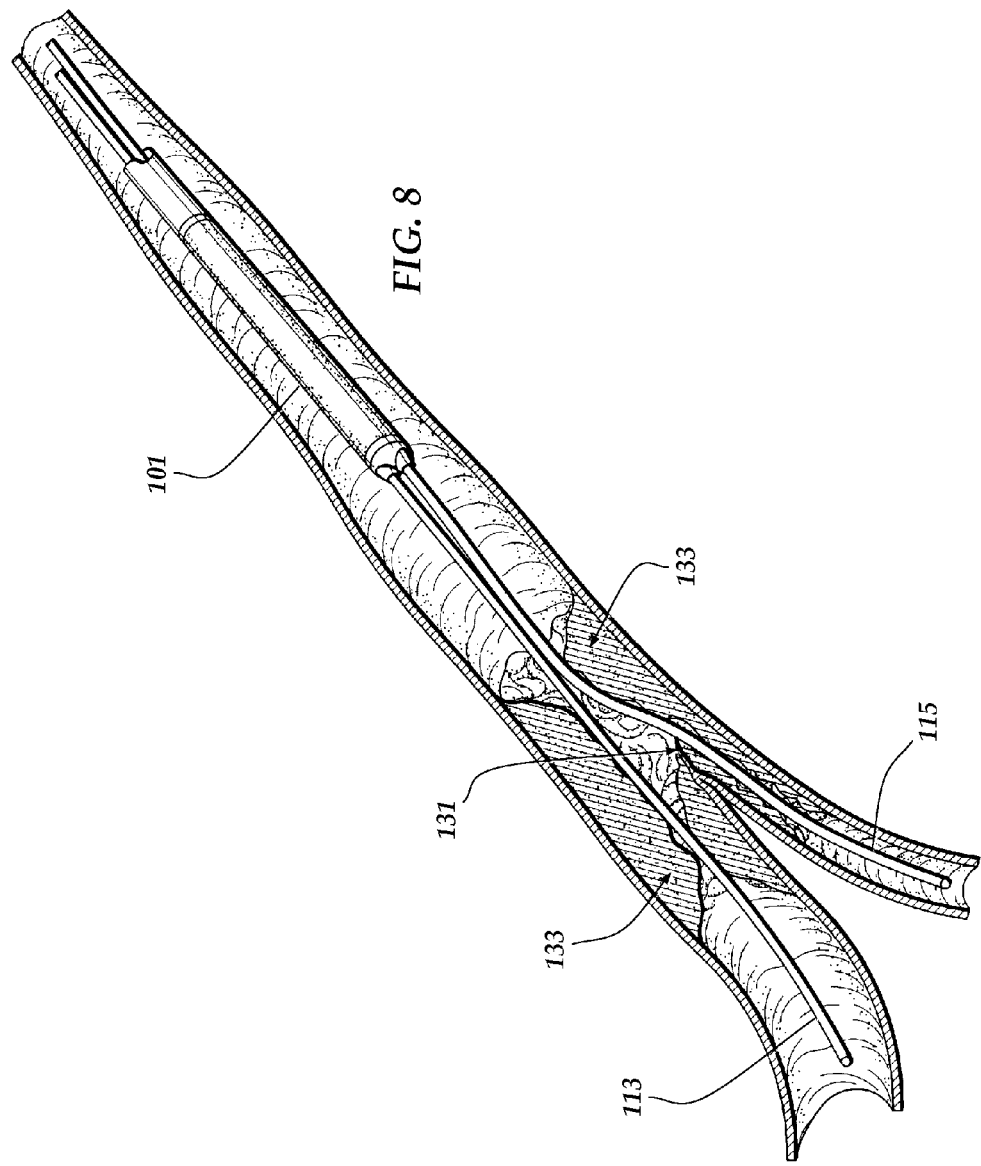

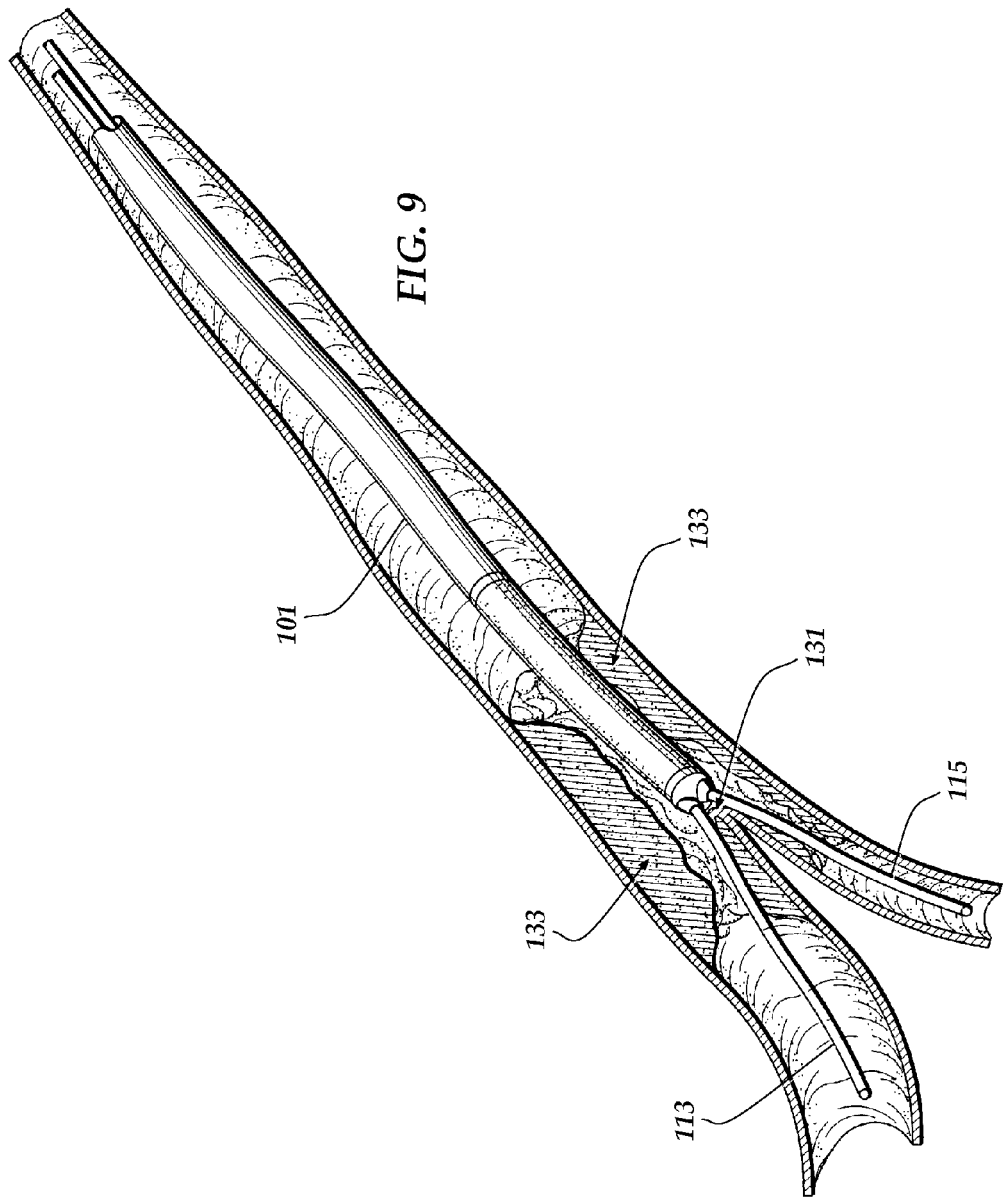

APPARATUS AND METHOD FOR TREATMENT OF BIFURCATION LESIONS

CROSS REFERENCES

None.

GOVERNMENTAL RIGHTS

None.

BACKGROUND OF THE INVENTION

The bifurcation lesion, particularly in the coronary arteries, is a challenging lesion to treat percutaneously. Each bifurcation lesion has a fingerprint-like uniqueness.

Treatment of bifurcation lesions is currently a topic of much investigation. Unlike most other lesion subsets utilizing bare-metal (BMS) and drug-eluting (DES) coronary stenting, the long-term results, particularly the incidence of restenosis, in either the main or subsidiary (side) branch vessel, after stenting the entire bifurcation are not necessarily better than stenting only the main branch and treating the subsidiary branch with balloon angioplasty. As such, provisional stenting, i.e., main branch stenting and stenting the side branch only when necessary, has been proposed as the preferred technique. Stenting of the side branch may be required in 30-50% of cases. There have been multiple methods proposed to treat bifurcation lesions. None have been shown to be more effective than single stenting alone, although several of these methods have not undergone extensive testing in controlled trials.

In the present specification, we propose a new device, and with it, new techniques to optimize treatment of bifurcation or trifurcation lesions. With this device and method, lesions will be treated more safely and more effectively, both in terms of immediate and long-term results, particularly in regard to the incidence of restenosis.

Conventional wire stents for treatment of blood vessel obstruction are used in conjunction with a catheter having an expandable member, or balloon, and a narrowed distal tip with a single guide wire emanating from the distal tip. In order to position the wire stent, the physician directs a guide wire into the diseased vessel and thereafter guides the catheter to the region of a diseased vessel; after proper positioning of the catheter and wire stent assembly, the physician expands the balloon to a predetermined diameter and thus implants the wire stent within the lumen of the blood vessel apposing it to the vessel wall. The physician may leave the guide wire in place throughout the procedure and thread additional catheters, wire stents, or balloon catheters over the guide wire, and the guide wire allows the physician to return to the same location without additional exploration of the vasculature. The catheter and guide wire are removed following treatment, and the vessel remains patent due to the reinforcement by the expanded wire stent. The wire stent should, in order to properly address the disease that led to the necessity of the treatment, overlay the circumference of the diseased portion and extend to a length beyond the margins of the diseased portion of the blood vessel.

When a catheter with wire stent assembly is used in the treatment of vascular disease in vessels for which there are no bifurcation branches involved in the vessel pathology, a single wire stent can be used with an expected low incidence of complications and with a high rate of confidence that closure will not occur immediately thereafter. However, in situations where the vessel disease occupies not only the main branch but also extends into a side branch, the use of conventional wire stents requires creative stent placement and balloon inflation of the side branch or a combination of more than one stent. In order to address circumstances involving bifurcation vessel disease, many researchers have proposed and designed very specialized and intricate wire stent and balloon assemblies that are designed to fit the bifurcation using angled wire stents or having special designs to allow for use in bifurcation lesions.

One prominent risk when treating bifurcation lesions is the potential for covering or occluding a side branch vessel when placing a wire stent into the main branch. Further, expanding the balloon in the main branch may force the plaque material into and seal the side branch through plaque shifting. Traditionally, when stents are required in both the main and side branches, the guide wire in one of the two branches must be removed and then reinserted through a cell in the previously implanted stent in the other branch. The lack of wire in one branch exposes that branch to closure and inability to rewire the branch or to further vessel trauma from attempts at reentry into the side branch. There is also evidence that implanting a wire stent in a vessel bifurcation can lead to blood flow turbulence which may stimulate growth of atherosclerotic plaque. It is thus an object of the present invention to avoid these complications and to avoid the problems associated with a physician's inability to locate or relocate a side branch or main branch during the procedure.

In order to address the above problems, physicians and researchers have described many methods to treat the bifurcation lesion and have provided a name for each method. Each is designed to use a number of conventional expandable wire stents to repair a bifurcation lesion. Mainly, the procedures are divided into various strategies in deciding which of the two branches to stent first, the main branch or the side branch. Furthermore, the type of balloons to be used varies by preference. Techniques such as the "Skirt," the "Crush," the "Culotte," the "Reverse Crush," the "Exaggerated Y," the "Minicrush," and the "Modified T" reveal the different ways that physicians have attempted to overcome the challenges of treating the bifurcation lesion using creative stent placement and balloon use.

There are four general categories of strategies used in current stenting technology for placing wire stents to treat bifurcation lesions. First is the insertion of a first stent in the main vessel close to the carina, in close proximity to the proximal main vessel. The initial step may also be followed by the opening of the stent towards both branches using the "Skirt" technique, followed by subsequent successive or simultaneous stent placement in one or both distal branches. A second strategy is to stent the proximal main vessel by positioning the stent across the side branch, thereafter reinserting a wire into the side branch and selectively enlarging a cell of the stent at the origin of the side branch vessel by inflating the balloon. Thereafter a stent may be implanted at the origin of the side branch if the origin of the side branch is sufficiently narrowed. The use of "kissing balloons" to fully expand both the main branch and side branch is useful in this second strategy. In order to perform this technique, the guide wire in the side branch must be removed with stenting of the main branch and then reinserted after main branch stenting. Thus, during this period, side branch access has been lost and must be regained, which is usually—but not always—possible. A third strategy is to stent the distal aspects of both branches using either a simultaneous stent placement at the ostium of both distal branches using a "simultaneous kissing stent," or a repetitive placement of a first stent in the distal main and a second stent in the distal side branch with final "kissing balloons." Another variant on this strategy is to use a "trouser legs and seat" approach whereby a first stent is placed in the main vessel distal to the carina, a second in the distal side branch, and a last stent in the main vessel proximal to the carina. In this "trouser legs and seat" approach, there is a lack of complete stent coverage of the area immediately surrounding the carina, and this lack of stent coverage may fail to repair the bifurcation to the fullest extent necessary. That is, the conventional wire stent may be placed proximal to, but not entirely occupy, the entire portion of the bifurcation area. This creates opportunity for additional vascular disease or higher blood flow turbulence in the region stimulating further atherosclerotic plaque growth. A fourth strategy is a variant of the previous three and begins by stenting a side branch first. This stent extends into the main branch which is crushed against one wall of the main vessel and a second stent is then implanted in the main vessel across the side branch vessel. Again, the use of final "kissing balloons" after placing a wire back into the side branch is recommended as part of this technique.

There are four common problems associated with the foregoing stent strategies. First is the situation where there is inadequate stent coverage of the diseased area. As discussed above, the "trouser legs and seat" approach is most susceptible to inadequate stent coverage, although each of the strategies may been demonstrated to be susceptible to inadequate coverage even when technique is considered to be optimized.

A second drawback to the foregoing strategies is that there is "too much" metal in certain areas of the bifurcation stenting involved with some stenting approaches. That is, in order to respond to the risks associated with the inadequate stent coverage of some techniques, other techniques by necessity have substantial amounts of metallic stent in certain areas of the bifurcation and in so doing, may change the flow dynamics of the blood in that area. That is, the laminar flow characteristics of a normal bifurcation are altered to increase the amount and area of turbulent flow and may lead to additional vascular disease or accumulation of obstructive plaque in the area and may predispose to acute or subacute stent thrombosis. As it is very desirable to retain laminar flow characteristics to the original vessel structure of the bifurcation, it is important not to oversaturate the bifurcation with too much metal at any particular point within the bifurcation. Furthermore, the use of stents that are designed for "one-shape fits all" may alter the natural bifurcation angle between the main branch and the side branch and increase the severity and area of turbulence in the bifurcation.

A third drawback for each of these procedures is the physician's inability to predictably identify the precise location of the side branch when working with the main branch, or vice versa. Most physicians rely upon visual inspection using contrast or radiological visual imagery to identify the origin of the side branch by tracing possible blood flow. As conventional catheters and wire stent delivery systems have only one distal tip through which only one guide wire extends, the physician must move and reposition the catheter approximating the best place to implant the stent during the process for treating bifurcation lesions. The use of a guide wire in the side branch allows for an approximation of the location of the carina between side and branches.

A fourth drawback, perhaps the most crucial in terms of safety of the procedure, is the need to reposition the guide wire into a side branch after already having placed an expandable steel stent in the main vessel. This maneuver exposes the side branch to lack of guide wire access for part of the procedure. It may be difficult in many lesions because it requires crossing a cell of the wire stent. Further certain angles of the side branch may increase the level of difficulty in crossing and this difficulty may be amplified if the side branch opening (ostium) is severely narrowed or totally occluded. Crossing into the side branch, in fact, may not always be possible, particularly if the side branch becomes occluded during implantation of the main branch stent or if the ostium of the side branch is highly blocked or if the angle between main branch and side branch is highly unfavorable. In situations where the side branch becomes occluded during the procedure, the patient is at risk of additional heart muscle injury to the tissues distal to the occlusion. It is therefore an object of the present invention to reduce the risk of complications by permitting a physician to utilize a single catheter yet manage two guide wires when identification of the main branch and side branch are most efficient, most visual.

The prior art has attempted to address the problems associated with proper placement of wire stents in or around bifurcation lesions. In order to assist the physician in locating the side branch when working on the main branch, there are several prior art efforts to modify stents and devices relative to treatment of bifurcation lesions beyond a mere strategy in the placement of conventional stents in or around bifurcation lesions. For example, U.S. Pat. No. 6,508,836 discloses an apparatus and method for stenting bifurcated vessels that is configured for implanting a wire stent in a side-branch vessel using an angled stent with an angulated portion that corresponds to the angle formed by the side-branch vessel at the main vessel. The apparatus disclosed in the '836 Patent also contemplates the use of a relatively traditional single wire system wherein the catheter has a distal tip from which a single guide wire extends. In addition to this single guide wire emanating from the catheter tip, a second control wire is designed into the apparatus to be used to torque and position the location of the main branch wire stent, such wire stent having an angled portion proximal to the distal tip of the catheter. The stated purpose of the second control wire is to identify the side branch vessel, target the side branch vessel, and use such second wire to torque and position the wire stent, as specifically designed for the main branch vessel prior to expanding the stent within the lumen of the main branch vessel. One clear limitation to the '836 Patent is the requirement that the second control wire emanate from the catheter immediately proximal to the location of the angle design of the main branch vessel stent. That is, the use of a second control wire is coupled with the function of rotating the wire stent into position, and the rotational properties of this design depend upon the second control wire exiting the catheter proximal to the balloon and angled stent surface. The '836 Patent has an alternative embodiment that provides the use of a second control wire that facilitates the positioning of the wire stent having an orifice in the midline region of the main branch wire stent, but this design requires the second control wire to have an exact location relative to a specific wire stent design in order to properly torque or rotate the wire stent into place in the main branch relative to the side branch vessel. Again, the stated purpose of this second control wire is to cooperate with a very specific and tailored wire stent design which allows it to be placed in the main branch of the vessel at the same time the second control wire allows the physician to locate the side branch vessel and rotate the specifically designed main branch vessel wire stent into proper position. In another embodiment of the '836 Patent, the inventor discloses the use of a "Y-shaped" wire stent that is configured around a dual Y-shaped balloon, or expandable member, as described by the inventor. The use of two guide wires as disclosed in the '836 Patent allows a physician to manipulate the very specialized dual balloon Y-shaped wire stent design into position at the bifurcation location. In the embodiments presented in the '836 Patent, all have a single distal tip through which a single wire is threaded, and the essence of the invention is to use guide wires to position highly specialized wire stent designs for use in a main branch vessel.

U.S. Pat. No. 6,955,688 similarly discloses the use of a two guide wire system whereby the single balloon catheter has a first distal tip having one guide wire and a second tip with a second guide wire that projects from the body of the catheter at a position slightly proximal to the balloon or expandable member. This second tip and second guide wire may assist the physician in positioning a stent associated with the first distal tip. In one preferred embodiment of the '688 Patent, this second tip with second guide wire encircled by another balloon may be releasably attached to the first distal tip using a locking ring. The stated alternative embodiment depicts a dual balloon Y-shaped catheter assembly to cooperatively stent a bifurcation. The catheter assembly disclosed in this alternative embodiment of the '688 Patent includes first and second expandable members that are configured to reside side by side (Y-shaped) and which are intended to spring apart for implanting two stents simultaneously. A locking ring is designed to assist in holding the two expandable members together until such time as the physician decides to separate the two for use in differing branches of the vasculature. This locking ring configuration confers a benefit of inserting only one catheter at the commencement of the procedure yet allows the physician to have two guide wires and two wire stents available to the physician to treat the bifurcation lesion. The embodiment disclosed in the '688 Patent has several disadvantages, however, as it has two balloons that are actuated using the single catheter lumen. That is, the physician must necessarily inflate two separate balloons at once, so the physician must be absolutely sure that both wire stents are in the proper place within two different vessels before inflating the balloon. This leaves no room for error, and instead increases the risk of error, as the improper placement of only one of the two stents at once could lead to catastrophic results. The '688 Patent is silent on whether there may be independent inflation means for each of the two tips such that if the physician does not wish to inflate both balloons simultaneously one could do so. The additional components needed to permit independent inflation of either tip would logically increase the diameter of the overall catheter to the same degree as having inserted two separate catheters in succession.

U.S. Pat. No. 6,221,090 B1 discloses a stent delivery catheter assembly designed for use with a torquing member, a tracking guide wire, and a positioning guide wire. The disclosure is for the use of a guide wire and a control wire to allow for rotation of a main branch stent mounted upon such catheter and expandable member into accurate position near the vessel bifurcation. One embodiment disclosed by the '090 Patent reveals a single guide wire at the distal tip of the device and a second control wire that is confined within a complex torquing member apparatus such that the second control wire exits the apparatus at a substantially 90 degree angle from the direction of the catheter and assists the physician in locating a side branch.

The prior art reveals widespread use of a single guide wire catheter system known as the "over-the-wire" and another system known as the "rapid exchange" system. The present apparatus and disclosure is useful in either catheter designs, or a combination thereof. The present invention contemplates the ability of a physician to adapt this system with the most flexibility rather than using a one-size-fits-all main branch wire stent design and a specialized device to help torque or rotate the main branch wire stent into place relative to the side branch. It is further an object of the present invention to allow a physician to remain flexible on which area of the lesion the physician deems is best to stent given the particular characteristics of the bifurcation lesion. That is, the present apparatus is not limited to the requirement that a side branch stent be positioned first. The invention is also not limited to one embodiment or use with only one commercially available catheter system but can instead be used with either existing over-the-wire or rapid-exchange catheter designs.

BRIEF SUMMARY OF THE INVENTION

The use of a catheter with single tip port through which a single guide wire is threaded has many limitations in situations involving bifurcated lesions. However, the use of a novel design disclosed herein that contemplates two or more guide wire ports at the distal tip of a single catheter permits the physician to manipulate the catheter with greater accuracy and reliability when treating bifurcation lesions in vessels. The use of two or more guide wires in conjunction with a single catheter allows the physician to begin the procedure by accurately locating the proper main branch and one or more side branches without having to thereafter remove a guide wire from any of the vasculature during the remainder of the procedure. This advance allows a much higher level of physician control over the procedure and permits the physician to revisit and confirm the integrity of the procedure without ever having to remove and reinsert a guide wire. The physician is also free to trust the guide wires will remain in proper position from the outset of the procedure and continuing through the duration of the procedure. Without guide wires, the physician runs the risk of occluding side branches or losing placement during the procedure. Once the several guide wires are in place and located in the proper region, the physician can then use virtually any commercially available catheter, balloon, and wire stent apparatus to treat the region. Alternatively, the physician may elect to thread more specialized catheters having various qualities and characteristics along the already-placed guide wires. The physician can also selectively insert tailored catheters along the already-placed guide wires throughout the procedure. That is, the physician may elect to insert a wire stent of a particular diameter along a first guide wire and thereafter or simultaneously insert a typical balloon or catheter having a different sized wire stent using another guide wire already positioned in, for example, a side branch vessel. The treatment of bifurcation lesions thus becomes less about trying to find the proper branches at various times throughout the procedure. The present apparatus and related methodology allows a physician to dedicate time and attention to using the full panoply of various stenting technology in an efficient and predictable way, by starting the procedure with the present apparatus that enable the physician to use multiple guide wires that are placed in the proper locations early in the procedure using one flexible apparatus. The proposed method of placement of stent placements is intended to improve long-term results by decreasing the severity of turbulent flow associated with all previously described methods.

The present disclosure also reveals how a specially designed expandable member, or balloon, can facilitate full coverage of the wire stents in areas immediately surrounding the carina of a bifurcation lesion using a tapered design.

These and other advantages will become apparent from the following detailed description which, when viewed in light of the accompanying drawings, disclose the embodiments of the invention.

BRIEF DESCRIPTION OF THE DRAWINGS

FIG. 1C is a perspective view of the catheter assembly having a plurality of guide wires and an expandable member for use in connection with a combination of rapid-exchange and over-the-wire systems wherein one or more guide wires exit from a section in the catheter assembly (rapid-exchange) and one or more guide wires exit from the proximal end of the catheter assembly (over-the-wire), and the proximal end has a port to inflate the expandable member.

FIG. 2 is a cross-sectional view of plane as further defined by Line 2-2 bisecting the expandable member region of the catheter depicted by FIGS. 1A, 1B, and 1C.

FIG. 3 is a perspective view of the distal area of the catheter assembly having a plurality of guide wires, expandable member, and an expandable wire stent surrounding the expandable member.

FIG. 4 is a side view of the distal area of the catheter assembly having a plurality of guide wires, expandable member, and an expandable wire stent surrounding the expandable member, with the plurality of guide wires exiting the distal end of the catheter in a substantially parallel fashion.

FIG. 5 is a side view of the distal area of the catheter assembly having a plurality of guide wires, expandable member, and an expandable wire stent surrounding the expandable member, with the plurality of guide wires exiting the distal end of the catheter in a substantially angled fashion, thereby illustrating a possible guide wire angle of incidence that may, upon preference, be present in one or more embodiments.

FIG. 6 is a perspective view of the catheter assembly having a plurality of guide wires, in this instance three, an expandable member, a silhouetted identification of the expandable member inflated diameter, and an expandable wire stent surrounding the expandable member.

FIG. 7 is a cut away perspective view of vasculature depicting a bifurcation lesion, such lesion having diseased occlusion in both branches. Shown here are the main and side branch vessels and two guide wires inserted in the respective branches.

FIG. 8 is a cut away perspective view of vasculature depicting two guide wires and a catheter through which both guide wires are threaded as the catheter assembly nears the bifurcation lesion, such lesion having diseased occlusion in both branches. Shown here are the main branch and the side branch vessels. Not shown is the presence of an expandable wire stent surrounding the expandable member, as it may be the physician's preference to insert a catheter with only an expandable member to ensure proper clearing of the occlusion before inserting the expandable wire stent in place.

FIG. 9 is a cut away perspective view of the insertion of an catheter having an expandable member (uninflated), as inserted along two guide wires as the physician directs the catheter to the carina, at which point the catheter cannot travel further. Shown here are the main branch and the side branch vessels. Not shown is the presence of an expandable wire stent surrounding the expandable member, as it may be the physician's preference to insert a catheter with only an expandable member to ensure proper clearing of the occlusion before inserting the expandable wire stent in place.

FIG. 20 depicts removal of the catheter, leaving a patent lumen created by the insertion of the second wire stent. Remaining in place are both guide wires.

LISTING OF COMPONENTS

101—catheter
103—proximal end
105—distal end
106—proximal connectors
107—expandable member
109—wire stent
111—conventional wire stent and single port catheter assembly
113—guide wire
115—second guide wire
117—third guide wire
119—guide wire lumen
121—pressurizing lumen
123—guide wire angle of incidence
125—expandable member inflated diameter
127—bifurcation lesion
129—blood vessel lumen
131—carina
133—plaque
135—main branch
137—proximal main branch area
139—distal main branch area
141—side branch
143—proximally tapered expandable member
145—distally tapered expandable member

DETAILED DESCRIPTION OF THE INVENTION

Figure 1A:
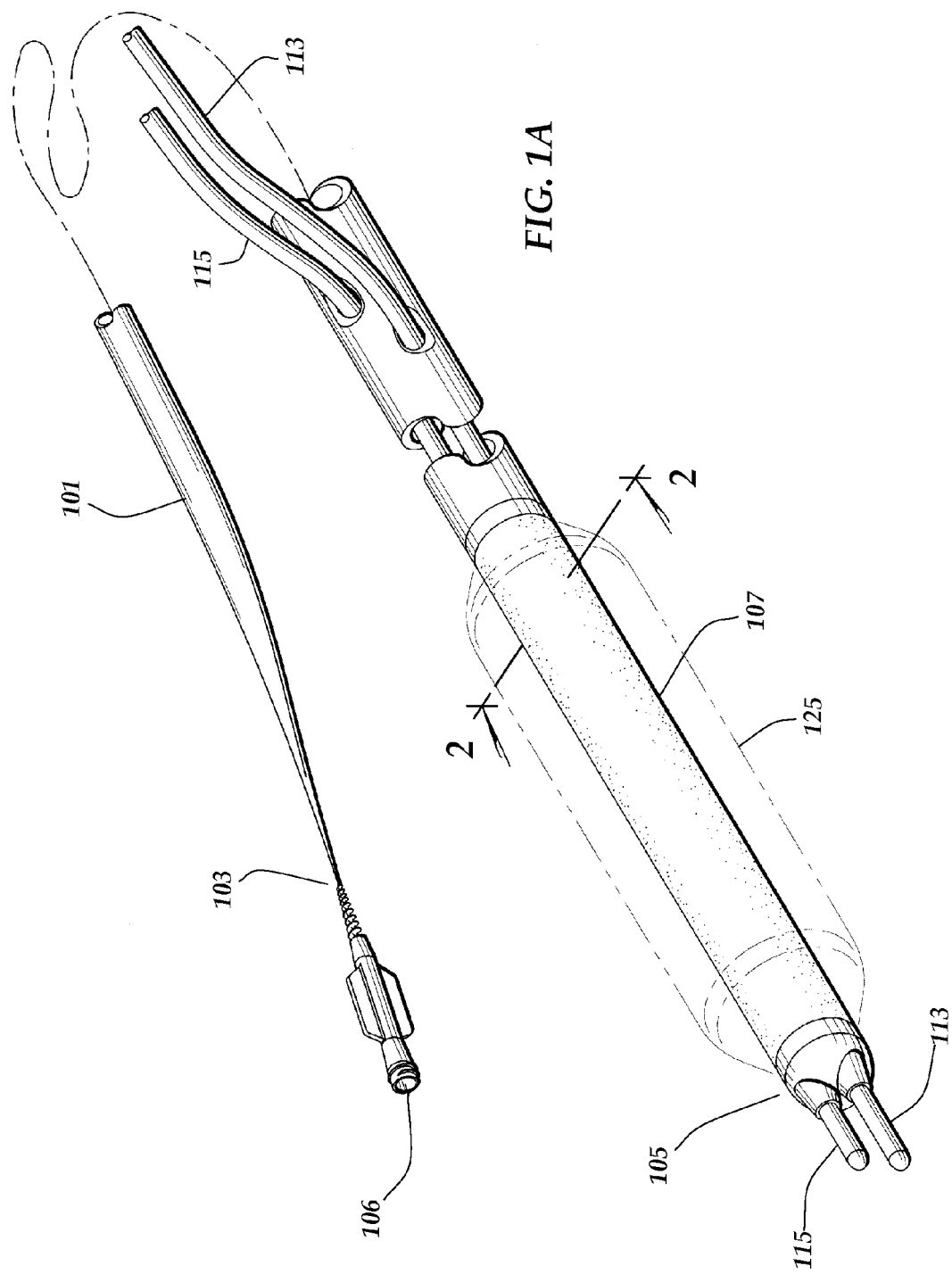
FIG. 1A is a perspective view of the catheter assembly having a plurality of guide wires and an expandable member for use in connection with a rapid exchange system wherein a plurality of guide wires exits from a section in the catheter assembly, and the proximal end has a port to inflate the expandable member.

The catheter 101 may have various embodiments. As shown by FIG. 1A, one apparatus may comprise a catheter 101 having a guide wire 113 and a second guide wire 115 located at a very short distal end 105 immediately distal to an expandable member 107. The catheter has as well a proximal end 103, and such proximal end 103 is located closest to the physician performing the procedure. The catheter 101 may have an expandable member 107, typically a plastic balloon of various formulations, very near the distal end 105, and at the distal-most region of the catheter 101, there is a distal end 117 through which guide wire 113 and second guide wire 115 extend. The catheter 101 may preferably also have an expandable wire stent 109 (not shown in this figure) surrounding the expandable member 107. The expandable member 107 is actuated, or inflated, to a predetermined diameter, shown as the expandable member inflated diameter 125. The means for inflation to the expandable member inflated diameter 125 is consistent with the increase in pressure along the pressurizing lumen 121 (see FIG. 2), which is ultimately controlled at the proximal end 103 of the catheter 101, using proximal connector 106. Shown in FIG. 1A are a first guide wire 113, a second guide wire 115, and an expandable member 107 for use in connection with a rapid-exchange system.

Figure 1B:
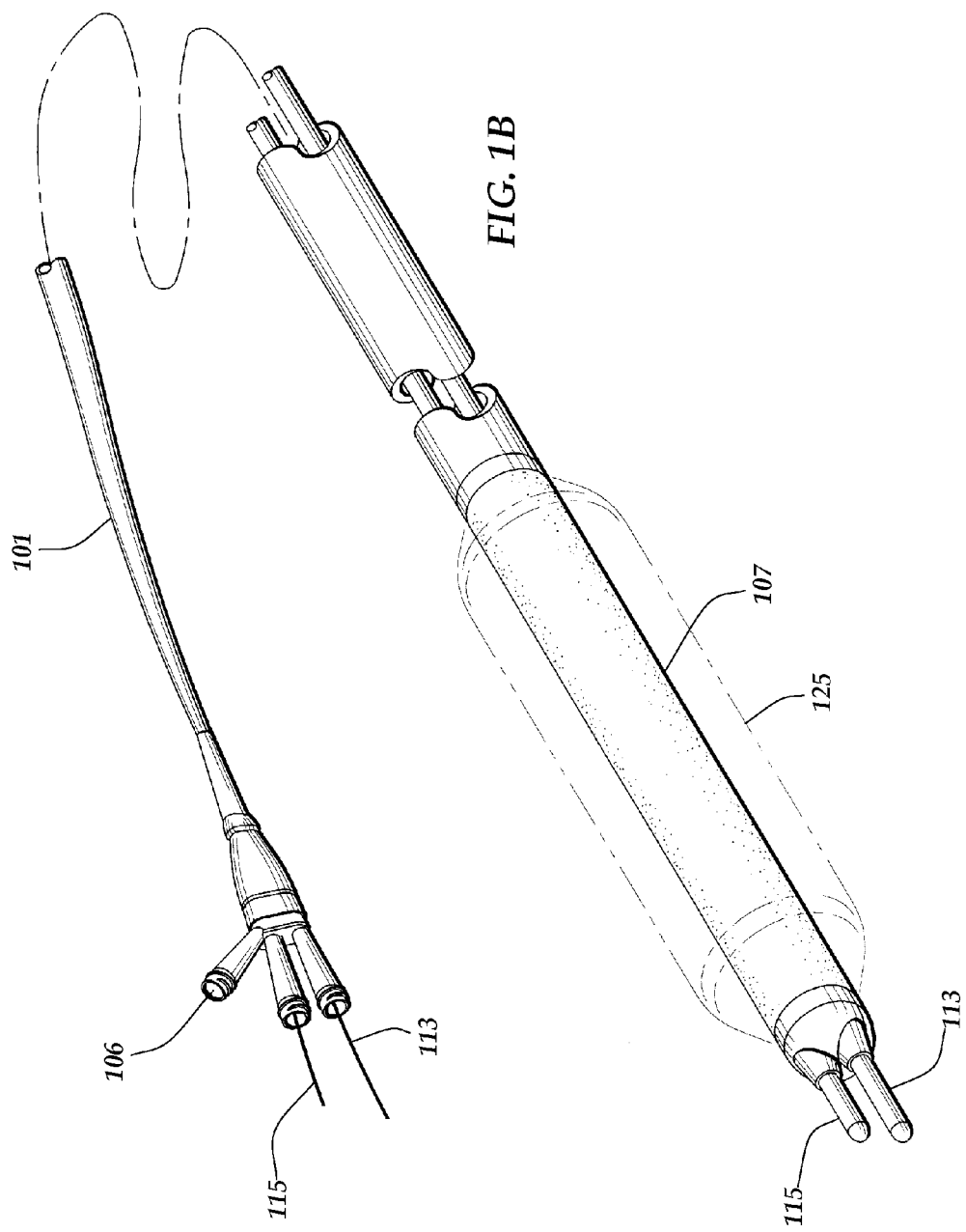
FIG. 1B is a perspective view of the catheter assembly having a plurality of guide wires and an expandable member for use in connection with an over-the-wire system wherein a plurality of guide wires exits from a section in the catheter assembly, and the proximal end has a port to inflate the expandable member, and a plurality of ports through which guide wires may be present.

A second alternative catheter design is shown by FIG. 1B, which is a perspective view of the catheter assembly for use in connection with an over-the-wire system wherein a plurality of guide wires exit from the proximal end of the catheter through guide wire lumens 119. Such proximal end also has a port to inflate the expandable member 107.

A third embodiment includes a combination system. FIG. 1C is a perspective view of the catheter assembly having a plurality of guide wires and an expandable member 107 for use in connection with a combination rapid-exchange and over-the-wire system wherein one or more guide wires exit from a section in the catheter assembly. In this third embodiment, one or more guide wires exit from the proximal end of the catheter assembly, and the proximal end has a port to inflate the expandable member 107.

The interior of the catheter 101, in any of the three embodiments, and as shown by cross-section along axis between 2-2 of FIGS. 1A, 1B, and 1C, allows for the plurality of guide wires to pass as sectioned with guide wire lumens 119, and such guide wire lumens 119 do not substantially interfere with the pressurization of the expandable member 107. The expandable member 107 can be inflated to a predetermined expandable member inflated diameter 125 by actuating the expandable member 107 by increasing pressure to the pressurizing lumen 121 using the proximal connector 106. FIG. 2 depicts the interior cross-section view of the catheter 101, as taken from the region involving the expandable member 107, as defined by axis between 2-2 of FIG. 1A. The cross-section of FIG. 2 reveals two or more guide wire lumens 119 and pressurizing lumen 121. This embodiment reveals the use of guide wire 113 and second guide wire 115 as located within respective guide wire lumens 119 and pressurizing lumen 121, all located within the confines of the catheter 101. FIG. 3 depicts the elements set forth in FIG. 2 in a perspective view, with the addition of the presence of an expandable wire stent 109 surrounding the expandable member 107. In view of the foregoing figures, the apparatus is substantially disclosed, as the catheter 101 may have an expandable member 107 that may, or may not, have a wire stent 109 associated therewith.

FIG. 4 is a side view of the distal area of the catheter 101 assembly having a first guide wire 113 and second guide wire 115, expandable member 107, and a wire stent 109 surrounding the expandable member 107, with the guide wires exiting the distal end of the catheter in a substantially parallel fashion.

FIG. 5 is a side view of the distal area of the catheter 101 assembly having a first guide wire 113 and second guide wire 115, expandable member 107 in non-expanded state, and an expandable wire stent 109 in non-expanded state surrounding the expandable member 107, with the plurality of guide wires exiting the distal end of the catheter in a substantially angled fashion thereby creating a guide wire angle of incidence 123. Upon preference, the guide wire angle of incidence 123 may be present in one or more embodiments.

FIG. 6 is a perspective view of the catheter assembly having a plurality of guide wires comprising a first guide wire 113, a second guide wire 115, and a third guide wire 117. Shown is a silhouetted identification of the expandable member inflated diameter 125, and an expandable wire stent surrounding the expandable member.

First Preferred Procedure Embodiment

In connection with the use of the foregoing apparatus, when used in connection with a percutaneous procedure, the physician may first begin the procedure by inserting guide wire 113 into the side branch 141 of a bifurcation vessel and a second guide wire 115 into the distal main branch area 137 of the bifurcation vessel. The order of wire placement is related to operator choice. The physician may insert the first guide wire 113 into the side branch 141 or the distal main branch area 137 beyond the plaque 133 occlusion. FIG. 7 depicts the first step, which comprises successively inserting two guide wires into the relative branches of the bifurcation lesion, the distal main branch area 137 and the side branch 141.

Figure 10:
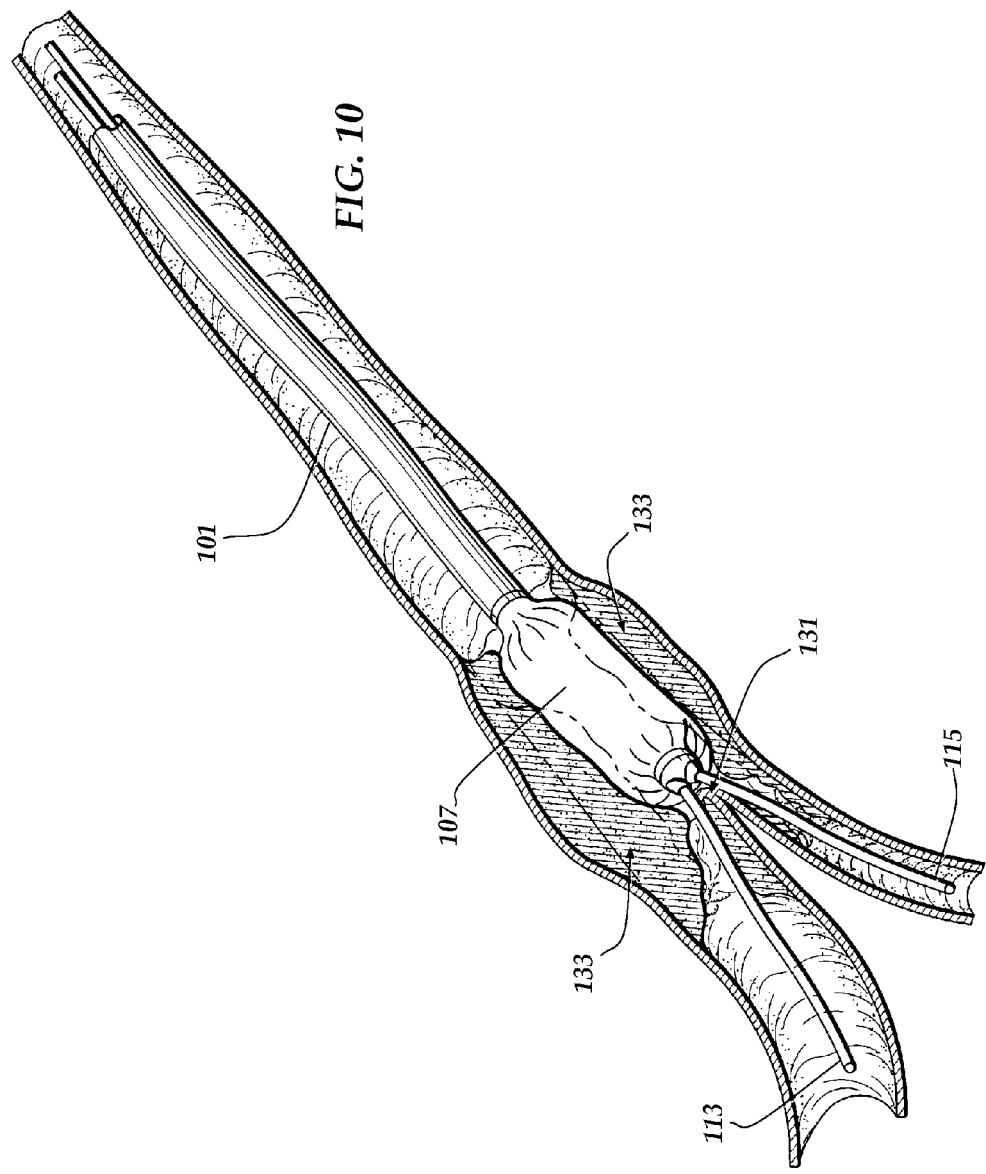
FIG. 10 is a cut away perspective view of the inflation of the expandable member after the catheter is in position near the carina. Shown is the displacement of the occlusion material from the proximal region on the main branch, recognizing that the inflation of the expandable member does not remove the existence of the occlusion or atherosclerotic plaque, but rather reforms and displaces the occlusion.
Figure 11:
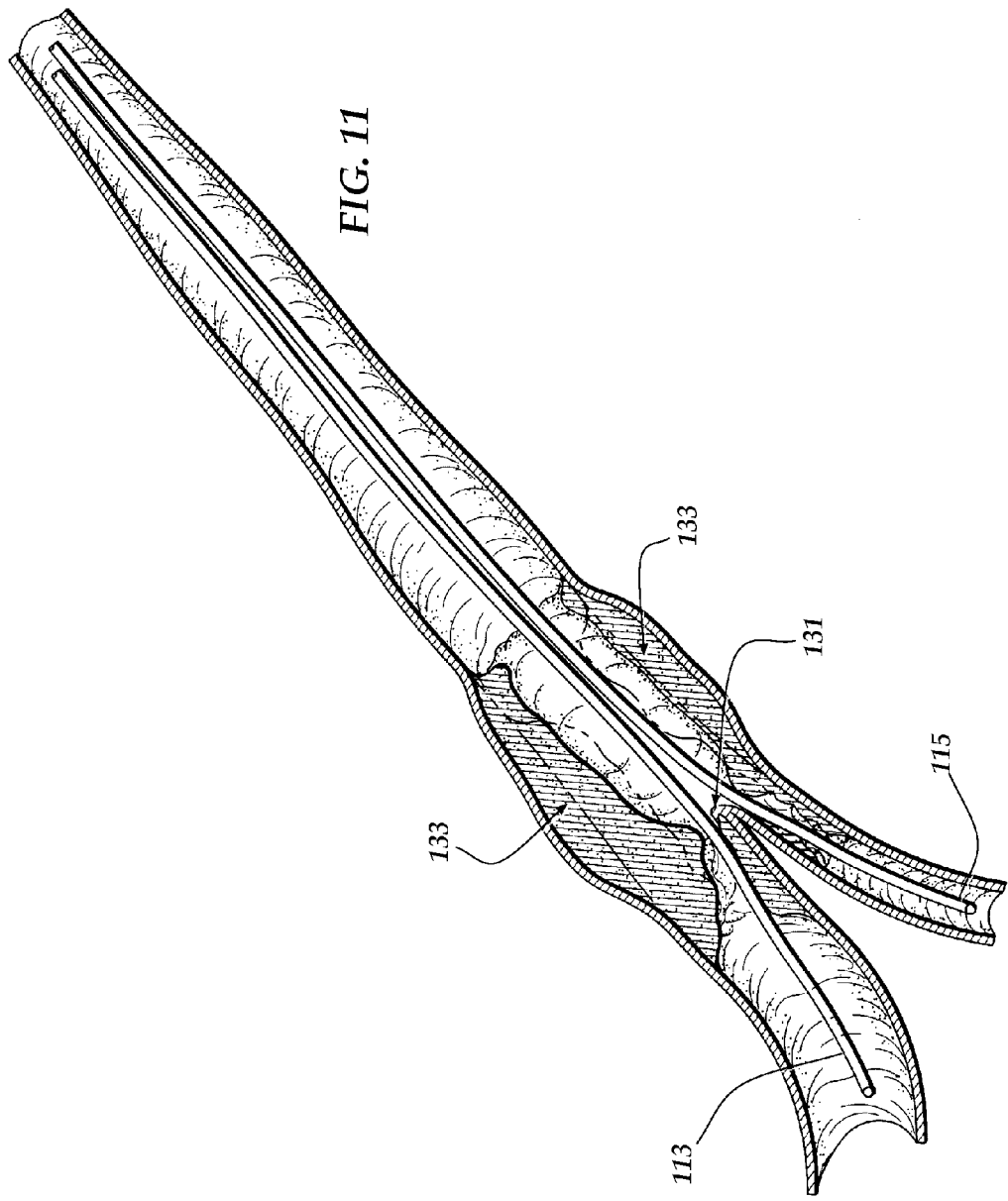
FIG. 11 is a cut away perspective view of the bifurcation lesion after when the catheter has been removed following inflation, in preparation for the insertion of a second catheter assembly, as circumstances warrant. Shown is the displacement of the occlusion material from the proximal region on the main branch, recognizing that the inflation of the expandable member does not remove the existence of the occlusion or atherosclerotic plaque, but rather reforms and displaces the occlusion. Also shown is the likelihood that inflation of the expandable member within the proximal main branch will further occlude the side branch, yet the placement of the guide wire in the side branch preserves the physician's ability to treat the side branch without interruption in the procedure.
Figure 12:
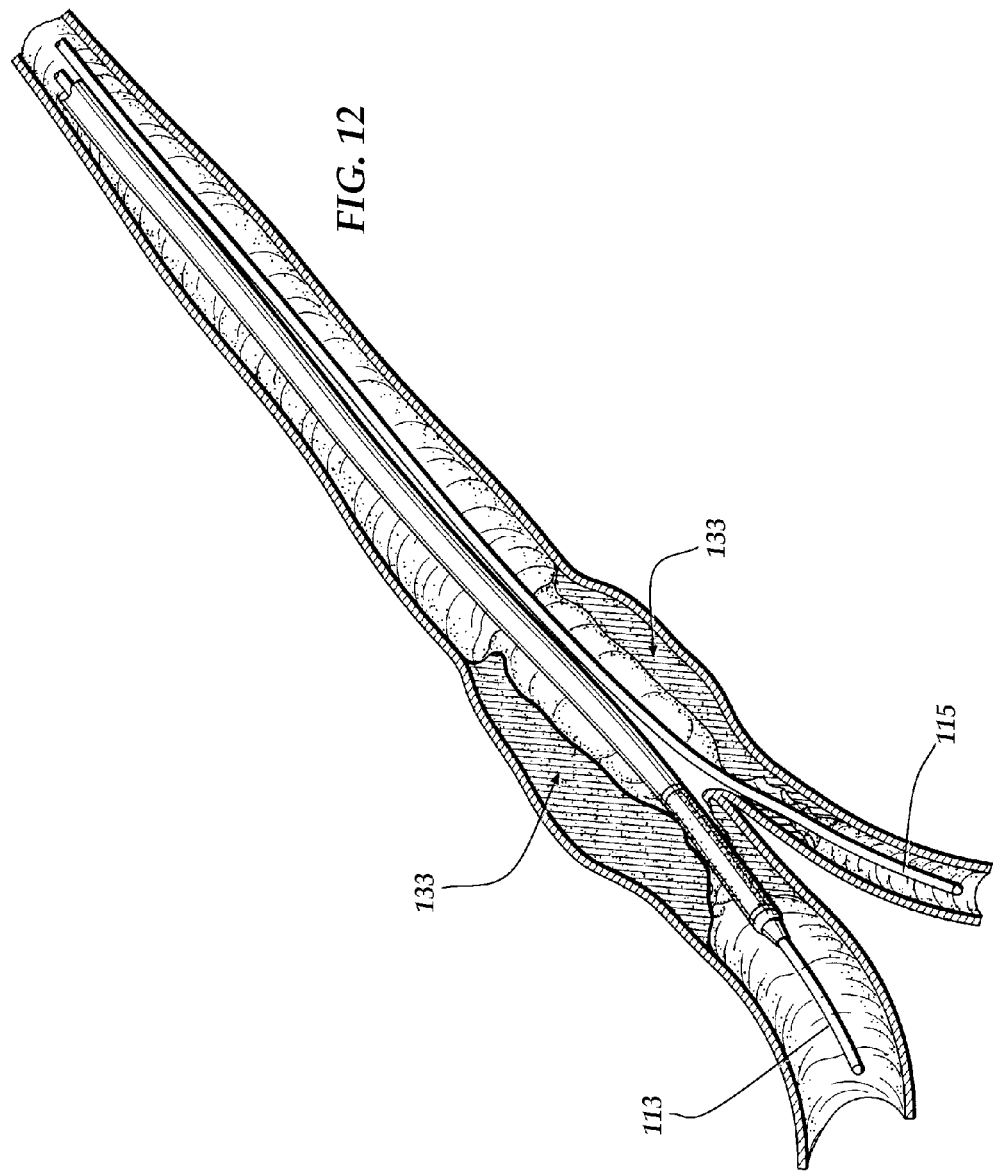
FIG. 12 is a cut away perspective view of the bifurcation lesion depicting the insertion of a single guide wire catheter having an expandable member along a guide wire placed within the distal main branch. Shown is the expandable member prior to inflation.
Figure 13:
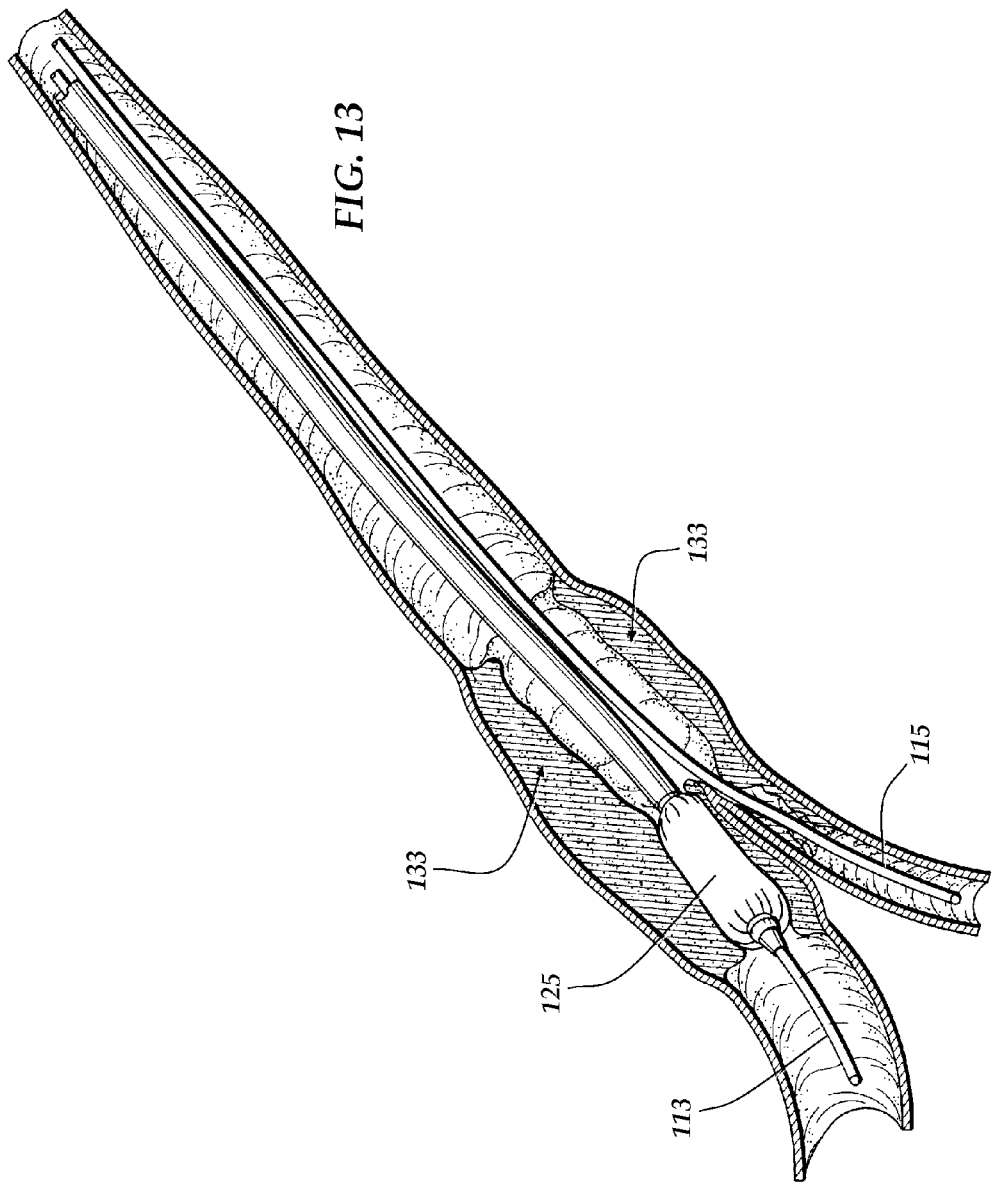
FIG. 13 is a cut away perspective view of the bifurcation lesion depicting the placement of a single guide wire catheter having an expandable member along a guide wire placed within the distal main branch. Shown is the expandable member during inflation and corresponding displacement or reformation of the occlusion material.

FIG. 8 depicts a successive step wherein the physician advances catheter 101 towards the carina 131 along both guide wires until arriving at the carina 131, as shown by FIG. 9. The physician may preferably insert a catheter 101 without a wire stent 109 in order to reconfigure the architecture of the vasculature prior to inserting one or more wire stents 109. Using the dual tipped catheter assembly, the physician can expand the expandable member 107 at the location near the carina 131, as depicted by FIG. 10. This method provides lesion reconfiguration in being as close to the carina as possible because the dual tipped catheter cannot travel any further. After reconfiguring the architecture of the lesion near the carina 131 using a balloon only, the physician may withdraw the dual tipped catheter 101 consistent with FIG. 11, and elect to advance along either the first guide wire 113 or second guide wire 115 a conventional single tipped catheter, inflate such catheter in the respective lumens of the branches of the vasculature, deflate such expandable member 107, and remove the single tipped catheter from the vasculature, all as depicted by FIGS. 12-16. FIG. 12 depicts insertion of a single tipped catheter along first guide wire 113 into the distal main branch area 139. FIG. 13 depicts reconfiguration of the architecture of the lesion near the carina 131 in the distal main branch area 139, as the expandable member 107 is inflated to its expandable member inflated diameter 125.

Figure 14:
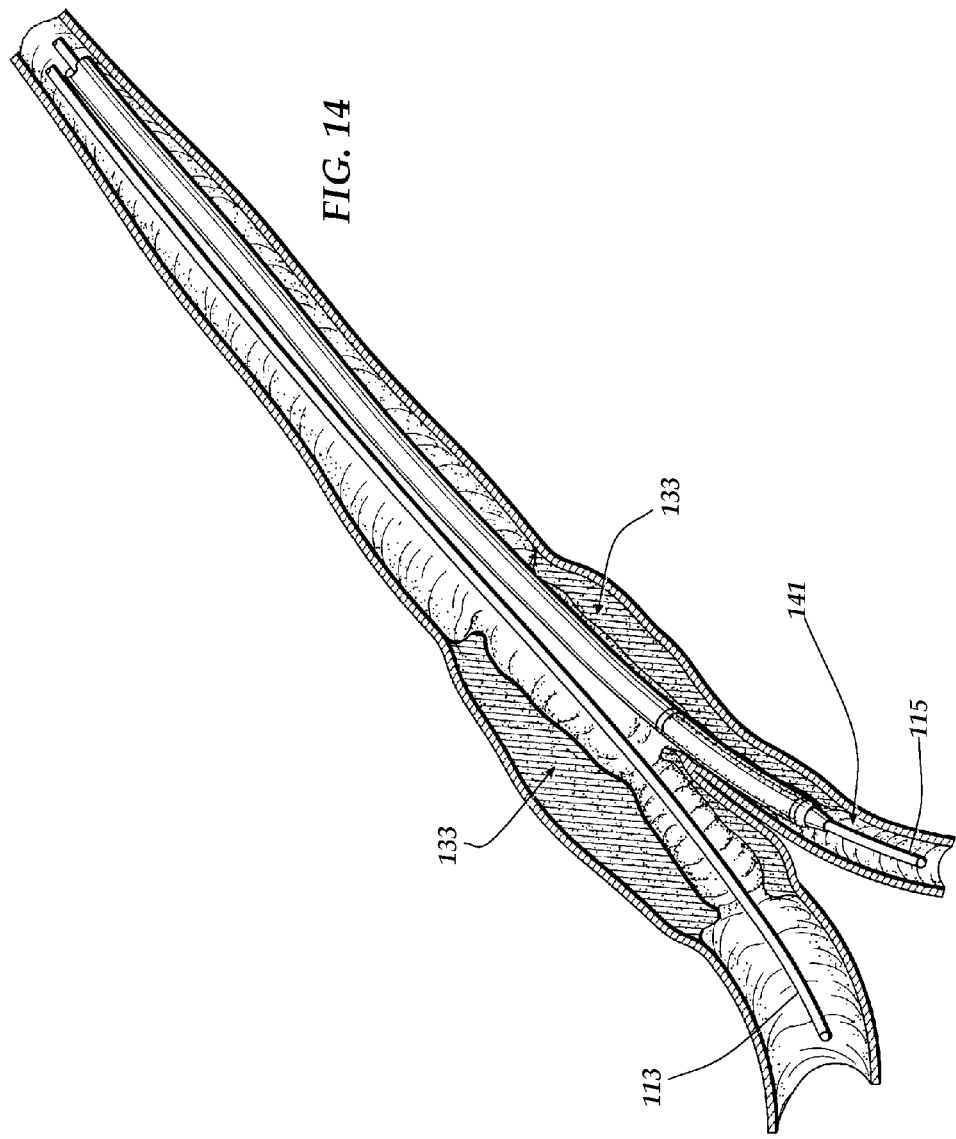
FIG. 14 is a cut away perspective view of the bifurcation lesion after the catheter has been removed from the distal main branch following inflation. Shown is the displacement of the occlusion material from the distal region on the main branch. The guide wire remains in place in the distal main branch.
Figure 15:
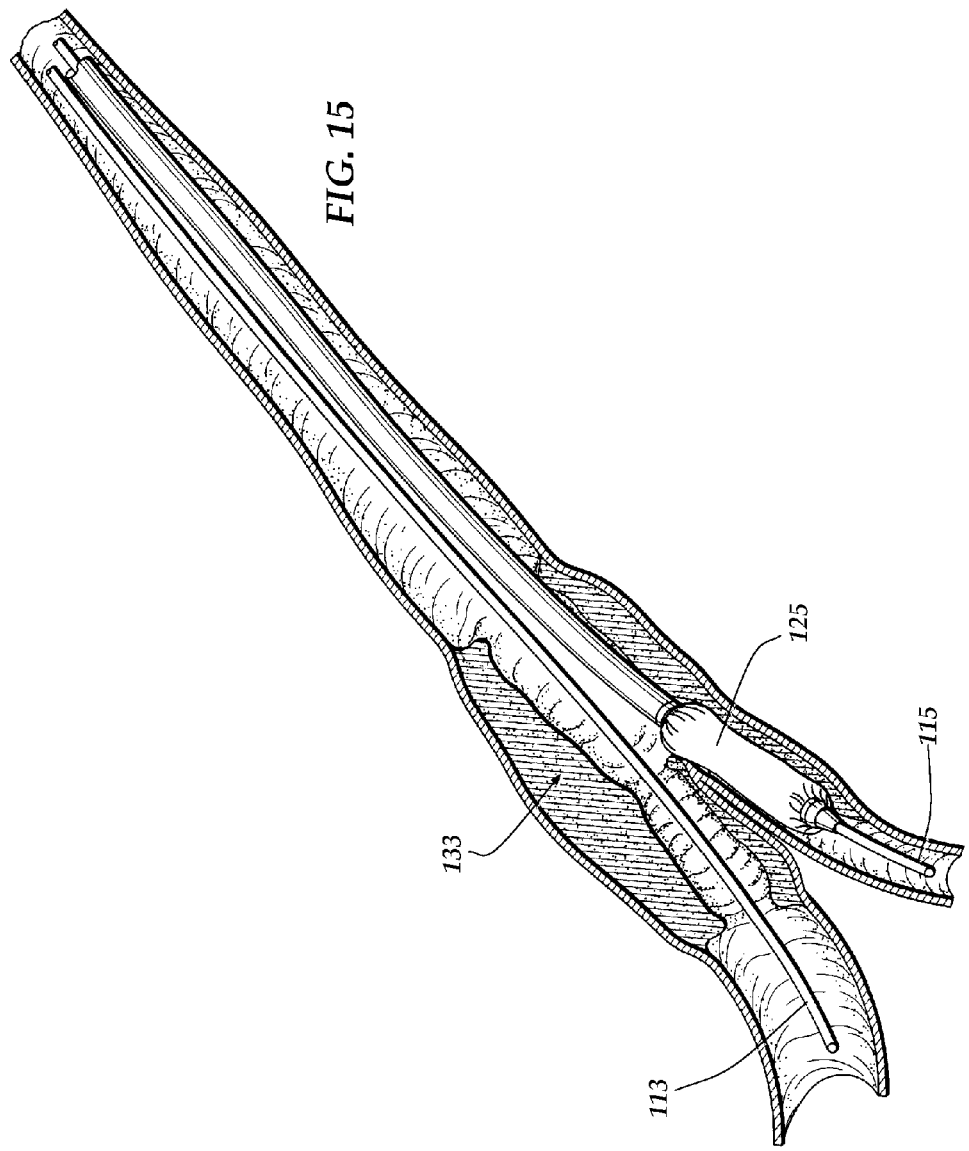
FIG. 15 is a cut away perspective view of the bifurcation lesion depicting the placement of a single guide wire catheter having an expandable member along a guide wire placed within the side branch. Shown is the expandable member during inflation and corresponding displacement or reformation of the occlusion material.
Figure 16:
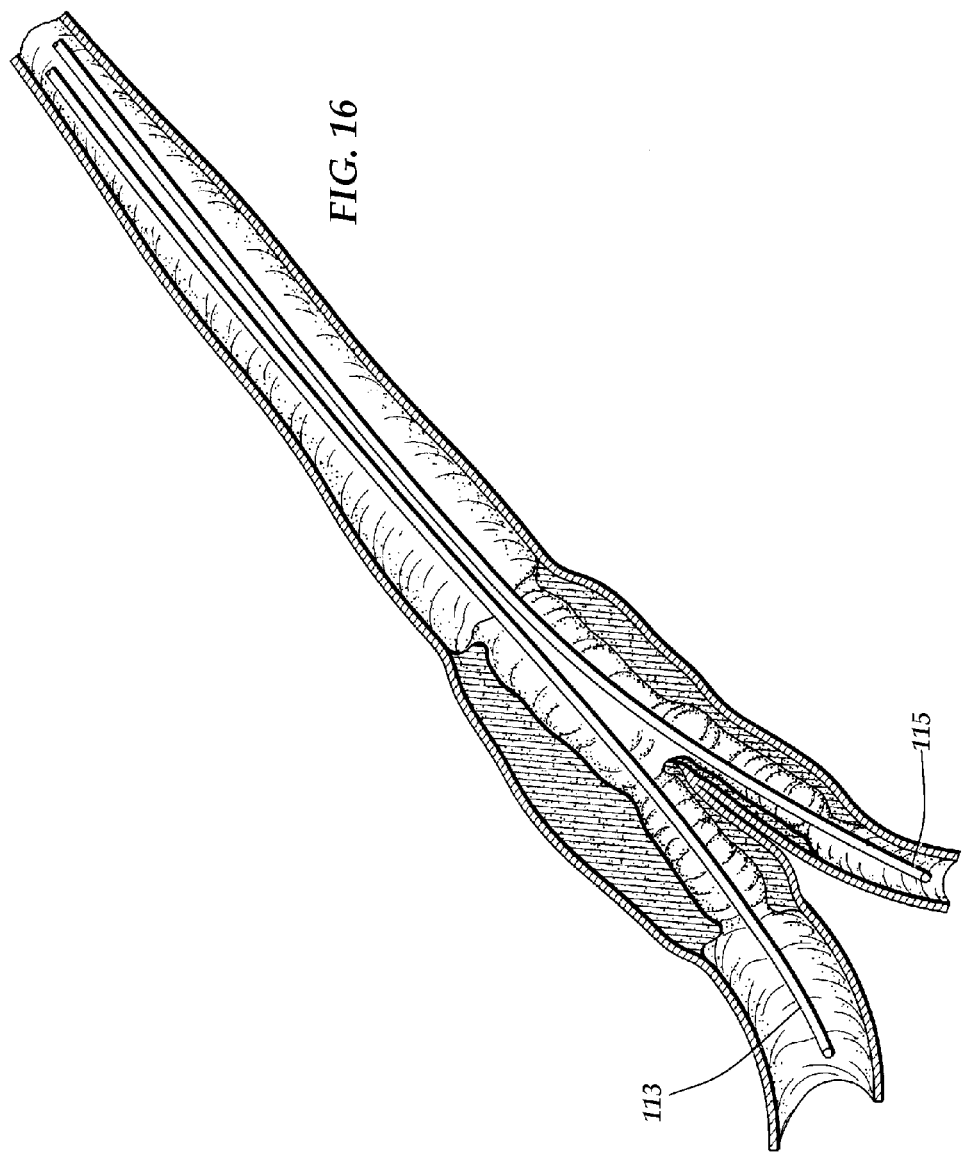
FIG. 16 is a cut away perspective view of the bifurcation lesion after the catheters have been removed from both the distal main branch and the side branch following inflation. Shown is the displacement of the occlusion material from the distal region on the main branch and the side branch, opening a substantial flow path. The guide wires remains in place in the distal main branch and the side branch.

FIG. 14 depicts insertion of a single tipped catheter along second guide wire 115 into the side branch 141, and FIG. 15 depicts inflation of the expandable member 107 to an expandable member inflated diameter 125 near the carina 131. FIG. 16 illustrates the benefits of reconfiguring the architecture of the lesion, having guide wires remaining in place. The plaque 133 is not removed using this procedure; it is reconfigured.

Figure 17:
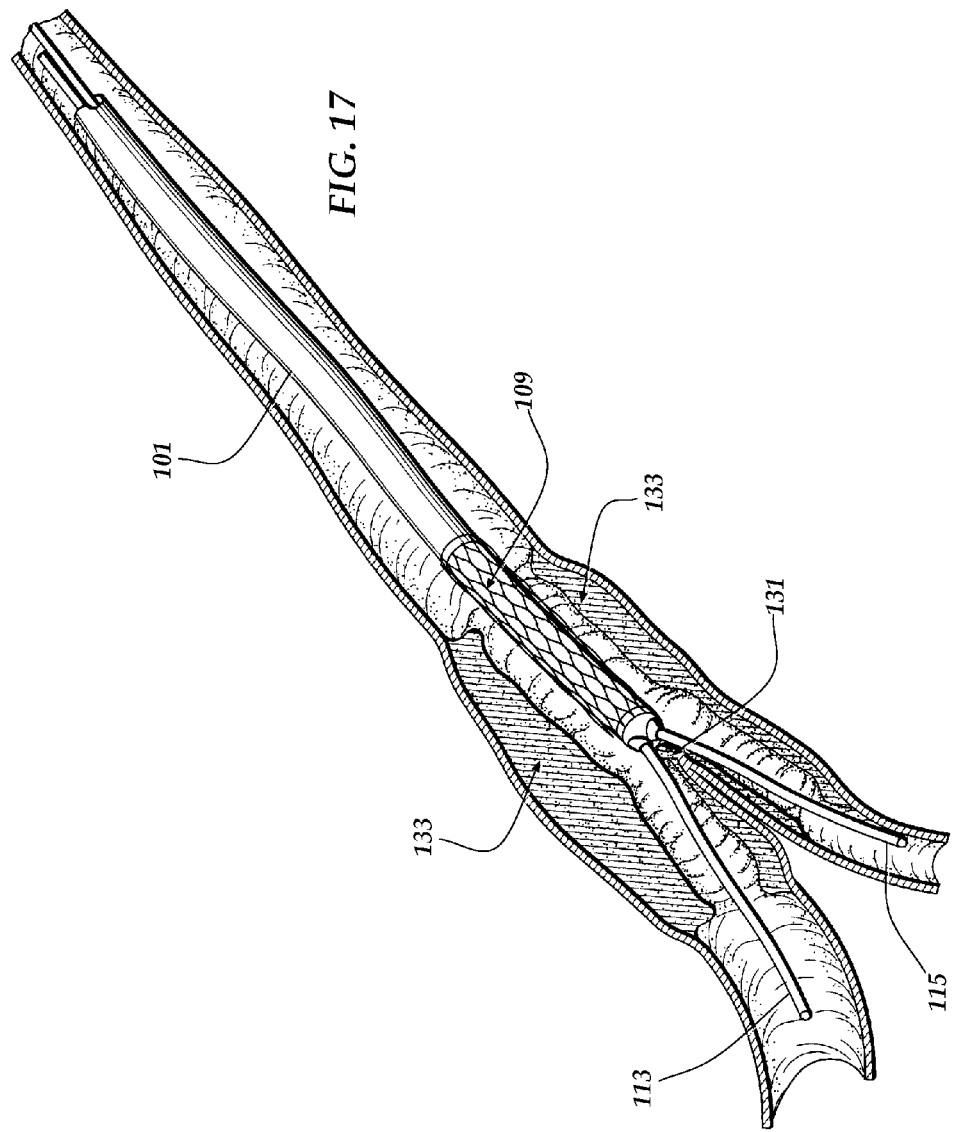
FIG. 17 is a cut away perspective view of the bifurcation lesion further depicting the insertion of the dual tipped catheter along the two guide wires. Both previously placed guide wires remain in proper location within the lumens of the side branch and distal main branch. The catheter assembly, in this depiction having an expandable wire stent surrounding the expandable member, is place, very near the carina. The expandable member is not inflated in this depiction.
Figure 18:
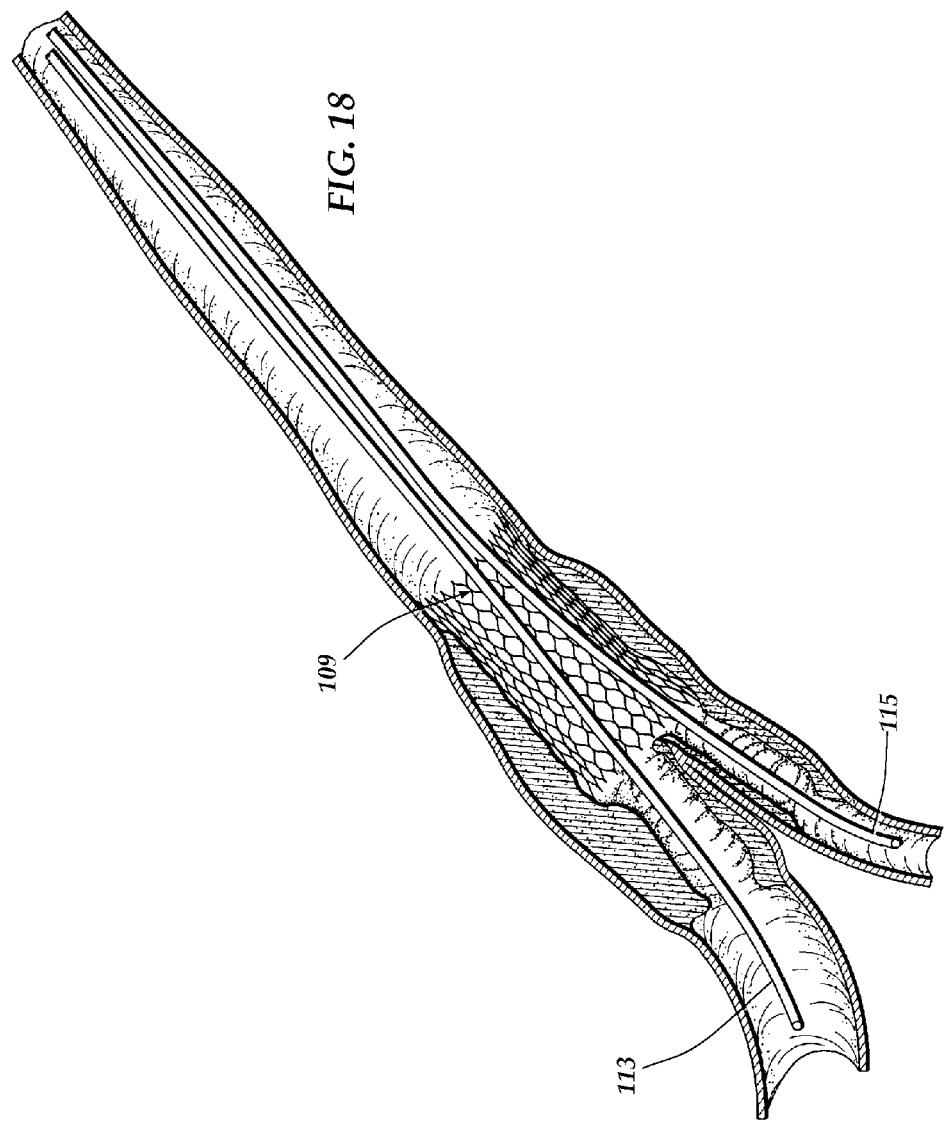
FIG. 18 is a cut away perspective view of the bifurcation lesion further depicting the removal of the dual tipped catheter from the two guide wires after inflating the expandable member, thereby placing the expanded wire stent in the proximal main branch region, near the carina. Both previously placed guide wires remain in proper location within the lumens of the side branch and distal main branch. Shown, too, is the additional displacement and reformation of the occlusion material, and the wire stent identifies new lumen parameters for the proximal main branch region. The wire stent adequately addresses the diseased lesion in this area.
Figure 19:
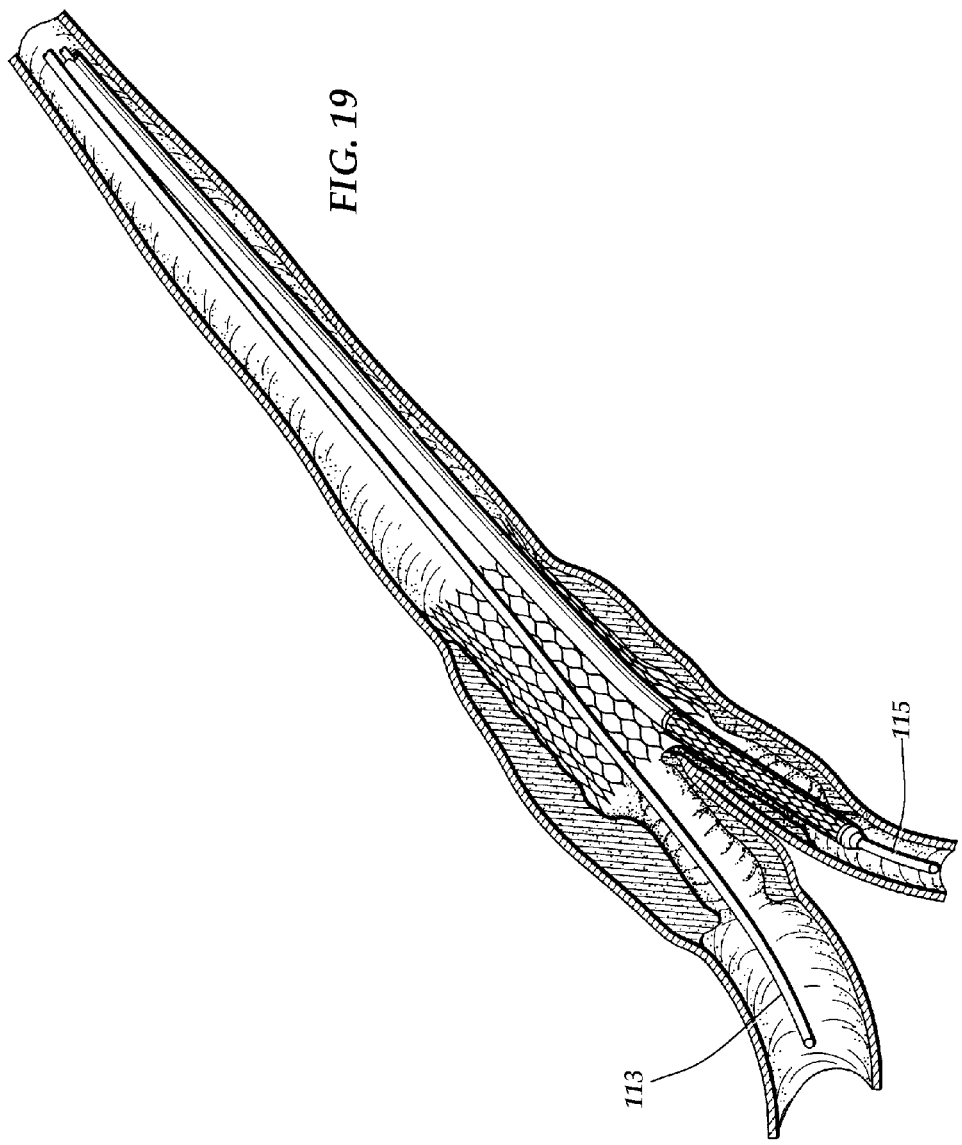
FIG. 19 is a cut away perspective view depicting the reinsertion along one of two guide wires of a first conventional single tip catheter assembly having an expandable wire stent surrounding an expandable member. The conventional single tip catheter is threaded along the guide wire previously positioned in the side branch. Undisturbed is the guide wire positioned in the distal region of the main branch vessel. Also shown by FIG. 19 is the maneuvering of a second expandable wire stent into the side branch in close proximity to the carina yet fully occupying the diseased region and displacing the occlusion.
Figure 20:
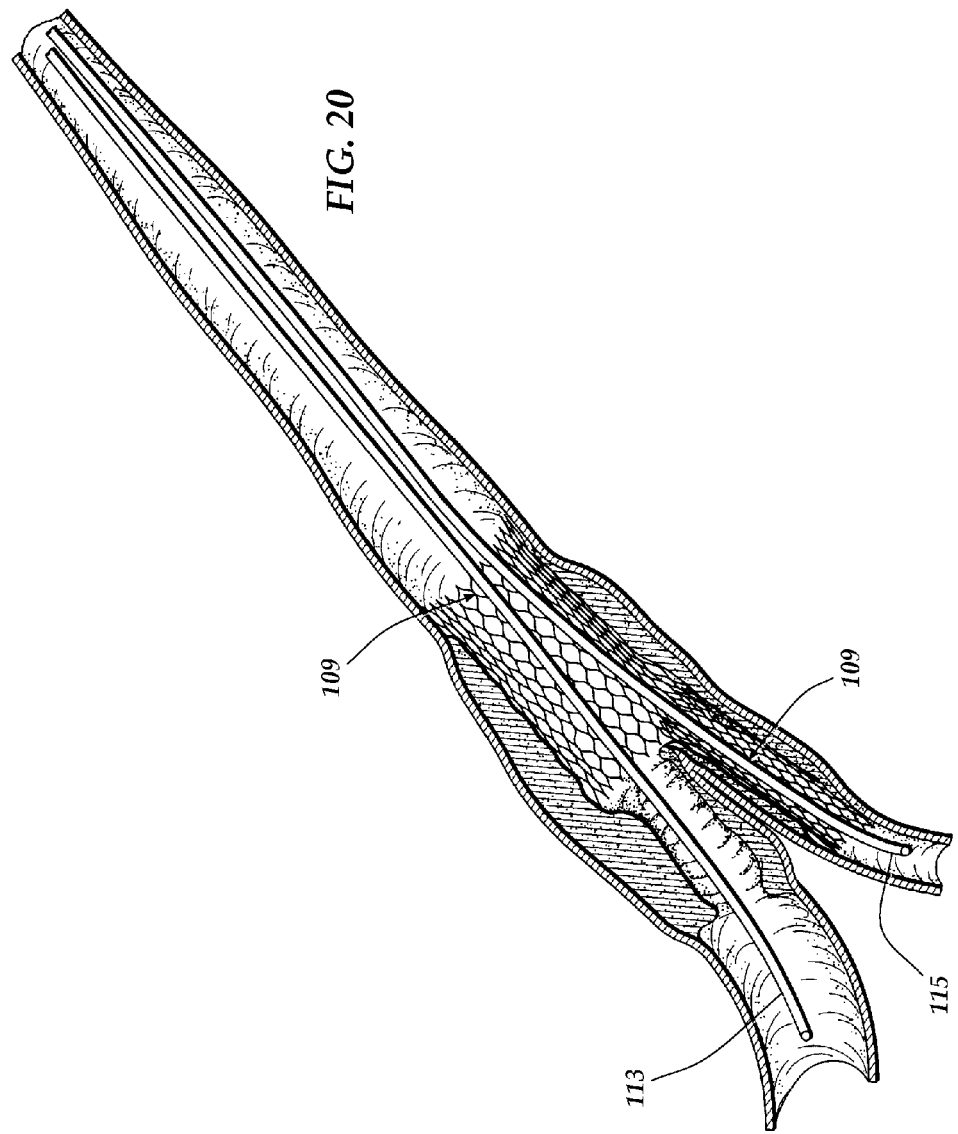
FIG. 20 is a cut away perspective view depicting the second expandable wire stent and catheter assembly in the side branch, as depicted by FIG. 19, having been positioned by the inflation and deflation of the expandable member.
Figure 21:
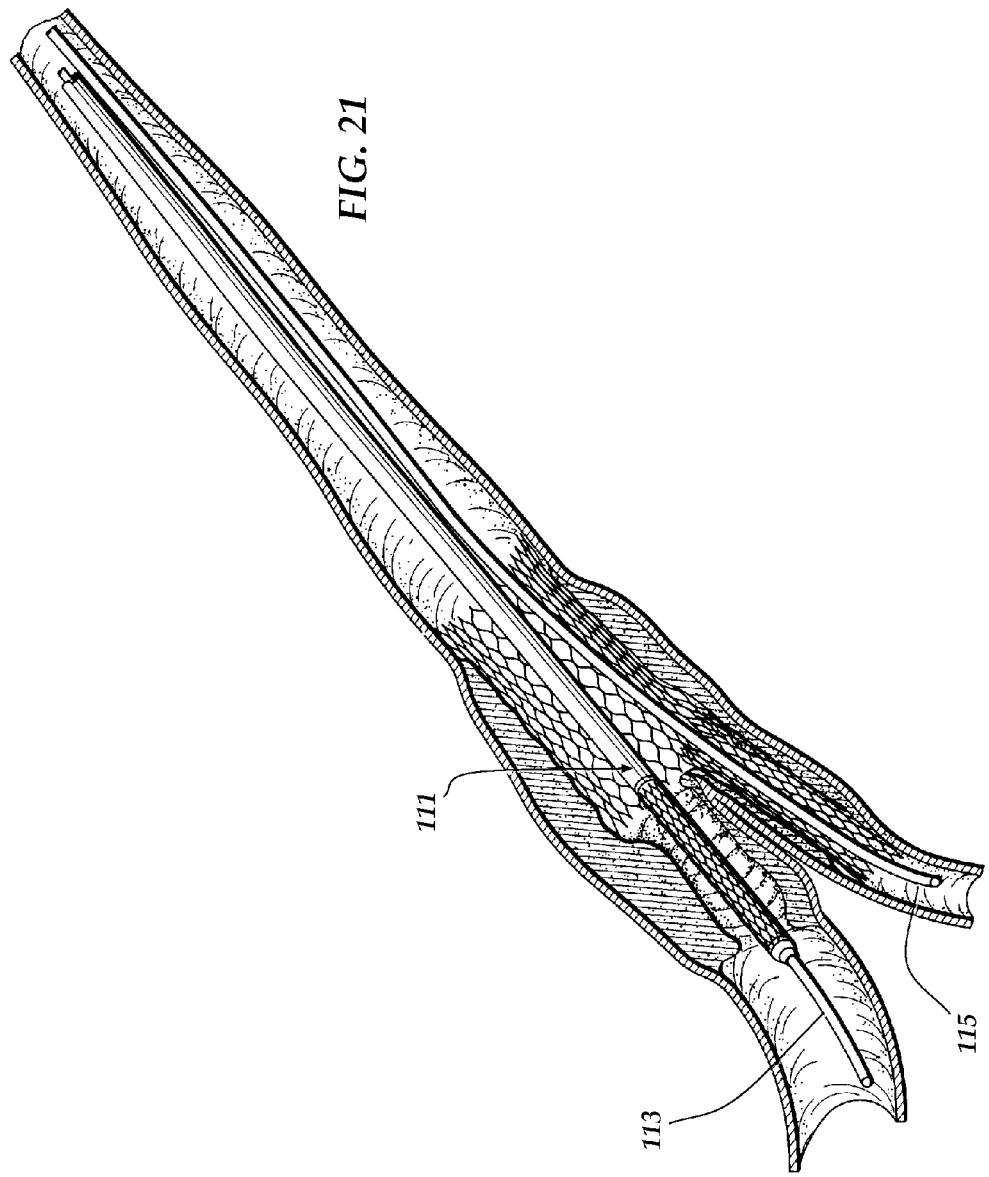
FIG. 21 is a cut away perspective view depicting the reinsertion along one of two guide wires of a second conventional single tip catheter assembly having an expandable wire stent surrounding an expandable member. The conventional single tip catheter is threaded along the guide wire previously positioned in the distal main branch. Undisturbed is the guide wire positioned in the side branch vessel. Also shown by FIG. 21 is the maneuvering of a second expandable wire stent into the distal main branch in close proximity to the carina yet fully occupying the diseased region and displacing the occlusion.
Figure 22:
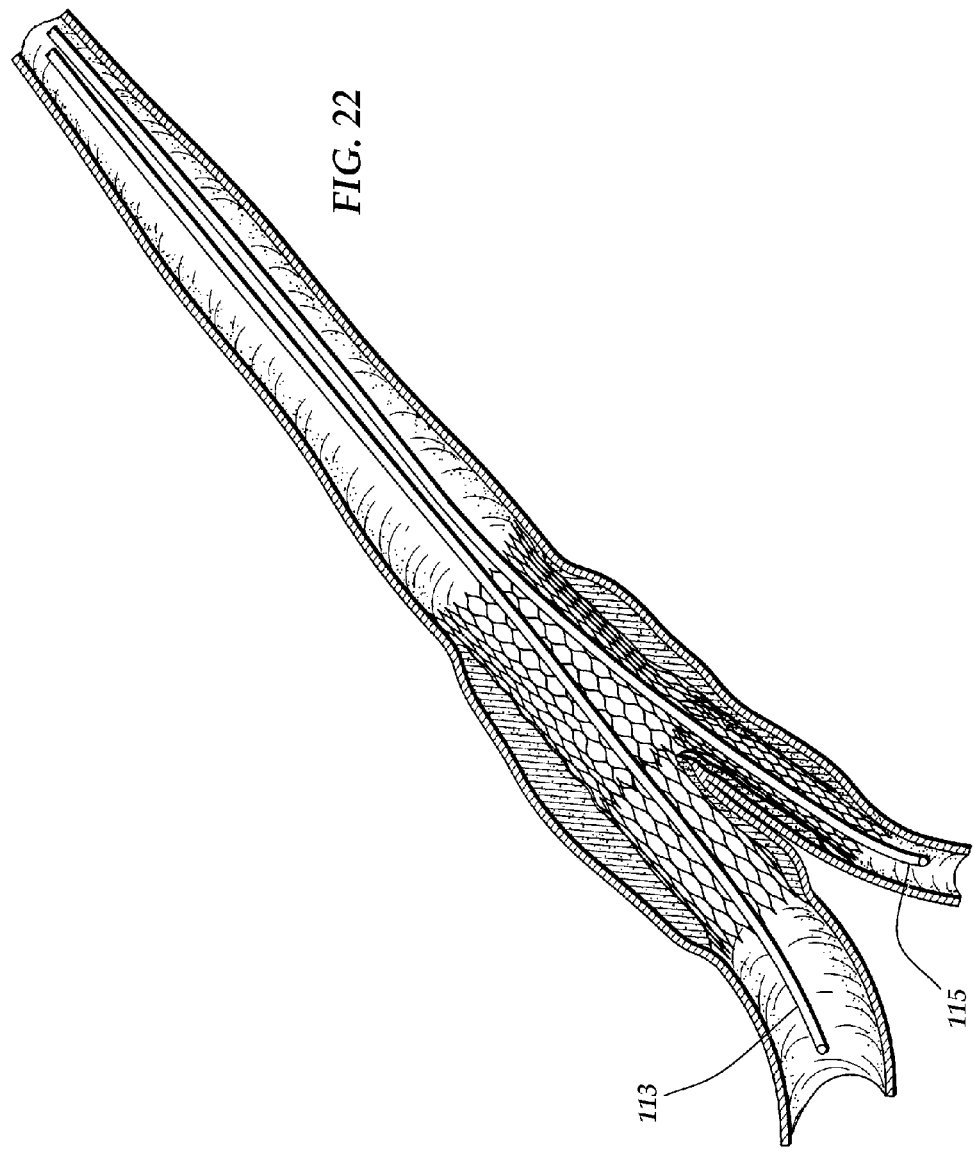
FIG. 22 is a cut away perspective view depicting the second expandable wire stent and catheter assembly in the distal main branch, as depicted by FIG. 21, having been positioned by the inflation and deflation of the expandable member. Remaining in place are both guide wires, so the physician has constant access to reinsert additional balloon catheters and/or wire stents as is necessary in order to fully and adequately treat the region. This view demonstrates how a physician using this apparatus and procedure may perform final testing on the accuracy of the stent placement and the integrity of the vasculature.

Subsequent steps to this procedure may comprise the use of wire stenting. If use of a wire stent 109 is clinically indicated, the physician can utilize the dual tipped catheter assembly with a wire stent mounted on the expandable member (balloon). As depicted by FIG. 17, the physician may simultaneously advance the dual tipped catheter having an expandable member 107 and wire stent 109 associated therewith along the first guide wire 113 and second guide wire 115 to the carina 131. Using the carina 131 as the end point, the physician is assured the placement of the wire stent 109 is proper and immediately adjacent to the side branch 141. Such placement, inflation of the expandable member 107, corresponding setting of the wire stent 109, and removal of the dual tipped catheter is depicted by FIGS. 17 and 18. The intended purpose of the placement of a first wire stent 109 near the carina 131 is to sufficiently occupy the proximal main branch area 137 immediately adjacent to the carina 131 and as close to the side branch 141 and distal main branch area 139 as possible. Having set the wire stent 109 in position by expanding the expandable member 107 to a predetermined expandable member inflated diameter 125 in the proximal main branch area 137, the physician can then elect to withdraw the catheter 101, leaving both the first guide wire 113 and the second guide wire 115 in relative position.

Thereafter, the physician can insert single tipped catheters having wire stents 109 surrounding the expandable member 107 into relative position in the proper branches of the vasculature. The repetitive and relative insertion, inflation, setting, and removal of the branch wire stenting using conventional wire stent and single port catheter assemblies 111 are identified in successive FIGS. 19-22.

Figure 23:
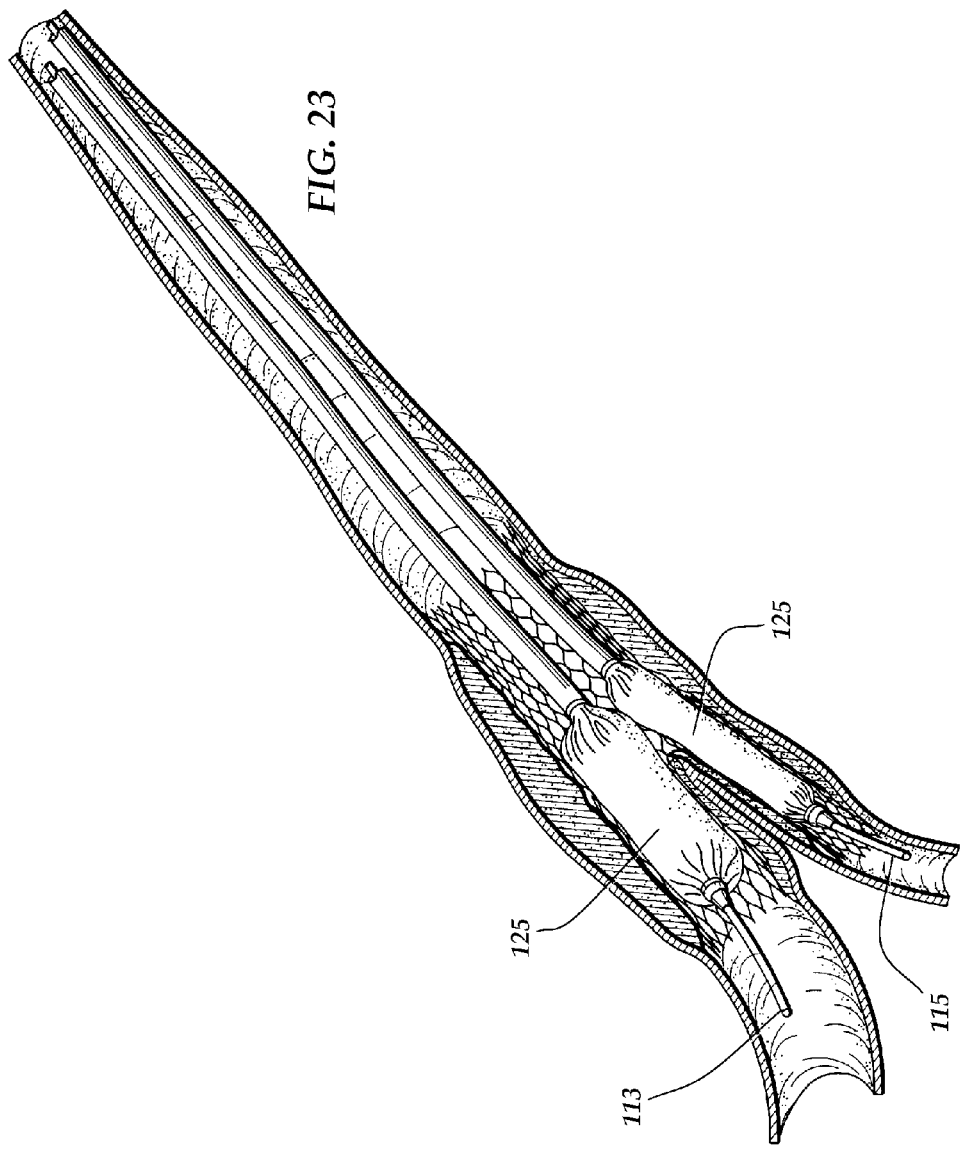
FIG. 23 is a cut away perspective view depicting the insertion of two single catheters having two separate expandable members along a respective guide wire and simultaneous inflation of such catheters ("kissing balloons") in order to finalize placement and apposition of the wire stents and insure good flow dynamics for the region.

At the physician's preference, the physician may simultaneously advance two single port catheter assemblies having only expandable members 107 but no wire stent 109 associated therewith into the vasculature using the first guide wire 113 and second guide wire 115 and simultaneously inflate ("kissing balloons") the expandable members 107 in order to make final configuration of the vasculature and three wire stents 109 in order to ensure the vasculature is patent and the wire stents 109 are well situated and apposed to all aspects of the carina and vessel wall. The foregoing is identified as FIG. 23.

Figure 24:
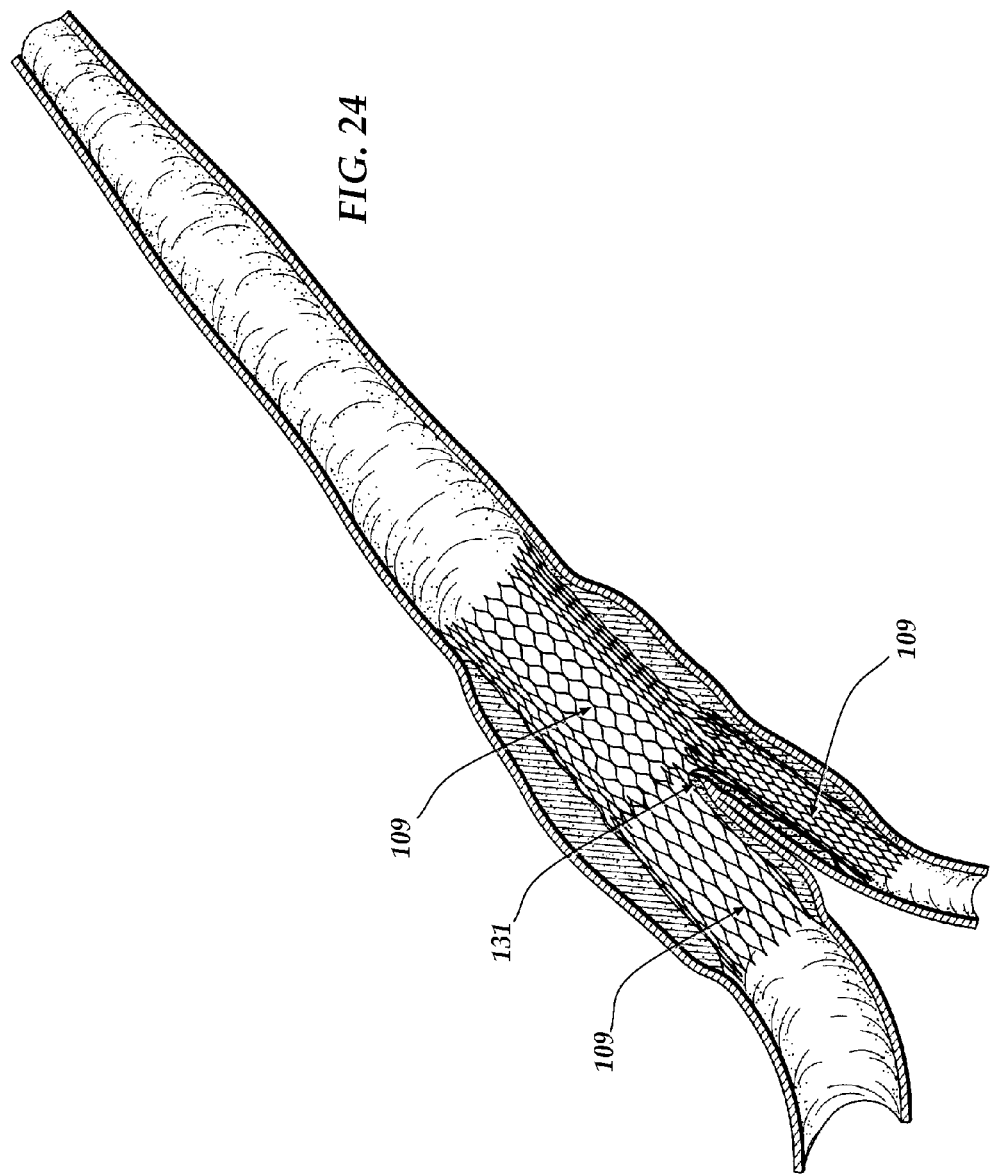
FIG. 24 is a cut away perspective view depicting the three wire stents in proper position at the conclusion of the procedure, both guide wires having been removed. There is total lesion coverage and minimal stent overlap, minimizing excess metal at any one point and maximizing normal flow dynamics.

FIG. 24 identifies the last step in the procedure, which is complete removal of the guide wires and all other instrumentation, leaving only the wire stents 109 in proper position near the carina 131.

Second Preferred Procedure Embodiment

Figure 25:
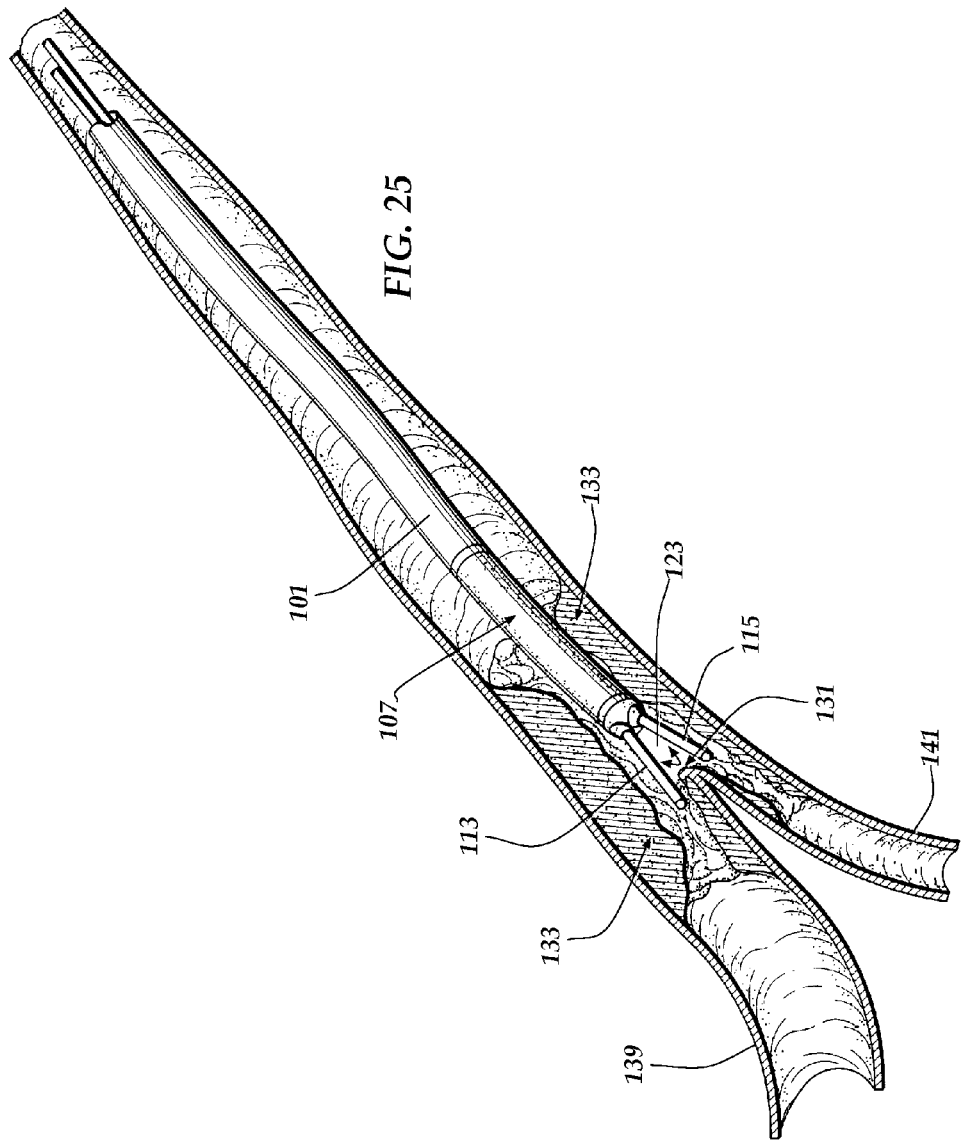
FIG. 25 is a cut away perspective view depicting an alternative use of the dual tipped catheter assembly, for use in conjunction with inserting the wire guides. Both guide wires are extended slightly along a predetermined angle of incidence as the physician nears the carina of the bifurcation. Depicted is the dual tipped catheter assembly with guide wires extending from the distal end.

Alternative to the foregoing procedure, a physician may use the dual tipped catheter assembly at the outset of the procedure to assist in the placement of the guide wires, as is depicted by FIG. 25. Helpful to this placement is the use of guide wire angle of incidence 123 created by a designed change in the angle by which the wire emanates from the distal tip. The procedure by which the physician would place two guide wires when using the apparatus disclosed herein may include advancing the catheter 101 into the side branch 141, over guide wire 113 into such side branch 141, withdrawing the catheter 101 to a point proximal to the carina 131 and advancing the second guide wire 115 into the distal main branch area 139. Assisting with this process may be a guide wire angle of incidence 123 that permits ease in advancing the second guide wire 115 into the distal main branch area 139 without erroneously advancing the second guide wire 115 into the side branch 141. That is, having first identified and located the proper area for the procedure, the physician may then place and leave guide wires 113 in the proper vasculature using a distal-to-proximal stepwise strategy. The strategy can use the main branch intubated first over the wire with withdrawal into the carina and passage of a second guide wire into the side branch utilizing the guide wire angle of incidence as an aid to guide wire intubation.

Next, the physician would retract the catheter proximally to a first carina and identify any proximal vasculature needing treatment and mark such vasculature with a second guide wire 115. Having a third guide wire 117 remaining in this example, the physician would then mark the most proximal vasculature with the remaining guide wire. Once each of the guide wires is placed in proper position, the physician would be free to either remove the catheter assembly 101 altogether or instead use the existing balloon or wire stent to begin treatment of the patient at the most proximal main branch area 137. That is, once all guide wires are in proper position, the expandable member 107 can be inflated and then deflated thus either reforming the occlusion architecture with expandable member 107 only or seating a wire stent 109 in the most proximal position and thereafter removing the first catheter, leaving all three guide wires in place. The physician may thereafter thread additional conventional wire stent and single port catheter assemblies 111 using any one of the three guide wires and successively treat the trifurcation lesion.

Optional Expandable Member Embodiment

Figure 26:
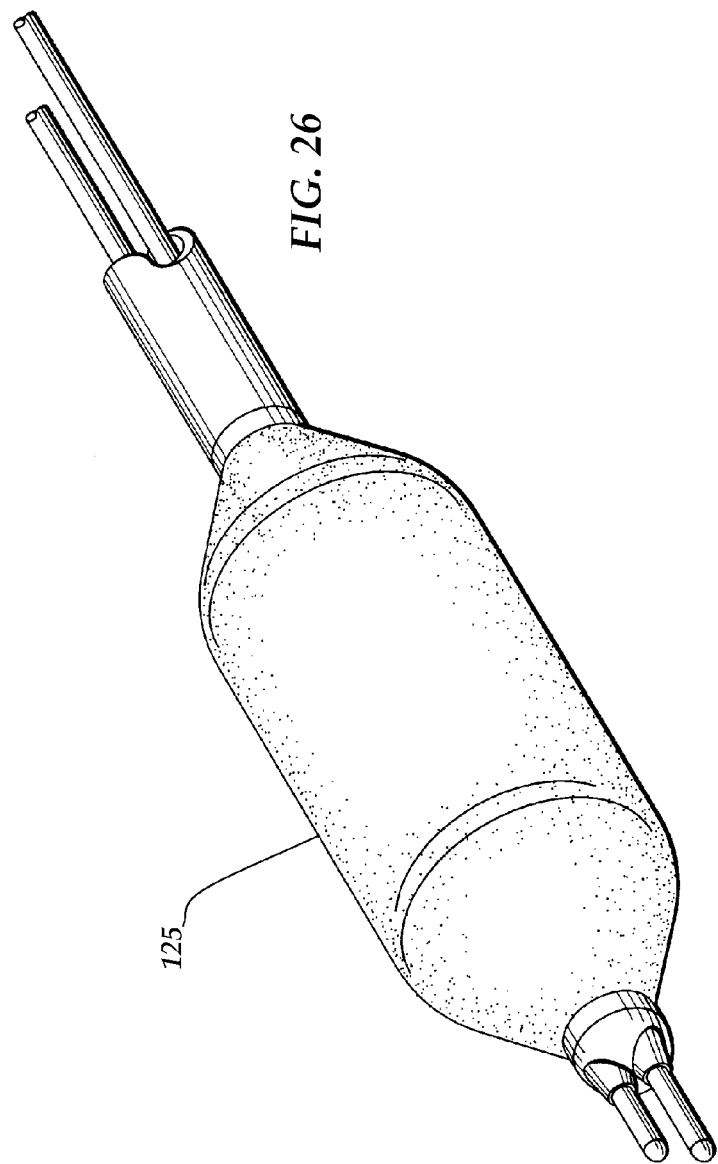
FIG. 26 is a perspective view of the distal end of a dual tip catheter assembly having an expandable member that is capable of inflating to a predetermined uniform expandable member inflated diameter.

FIG. 26 is a perspective view of the distal end of a dual tip catheter assembly having an expandable member that is capable of inflating to a predetermined uniform expandable member inflated diameter.

Figure 27:
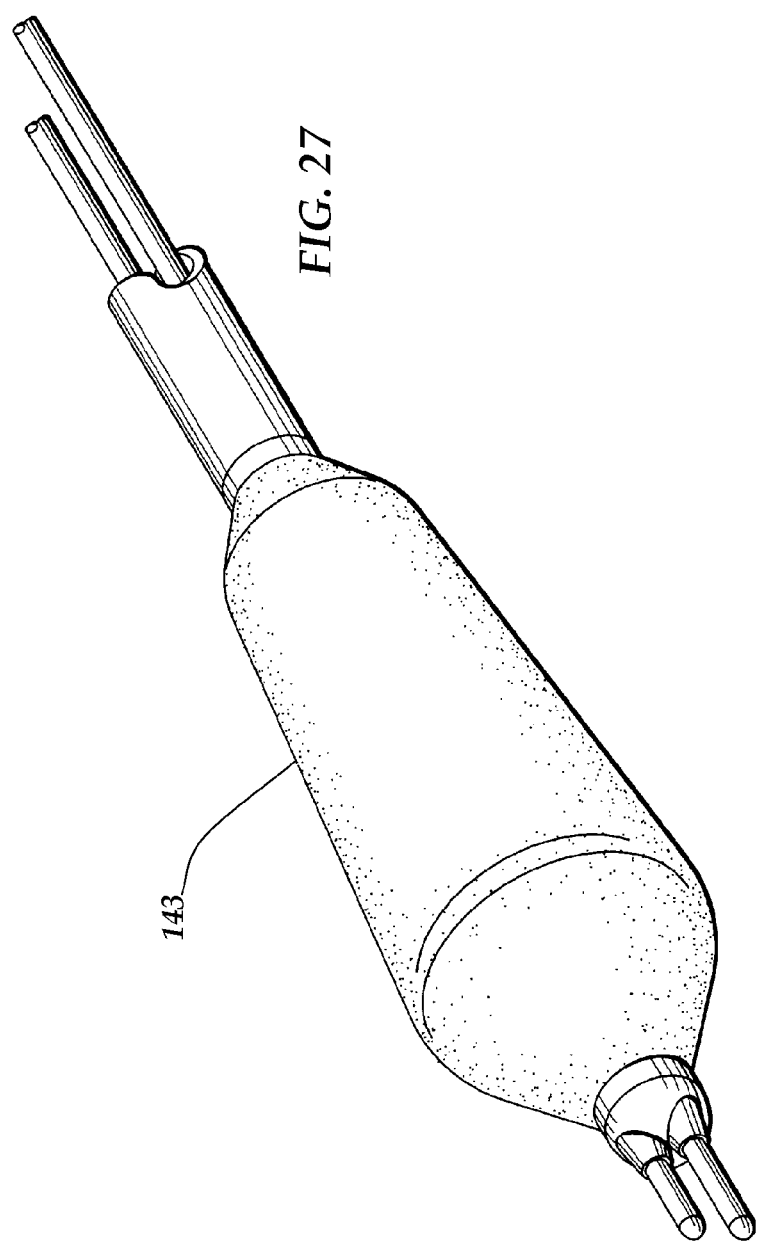
FIG. 27 is a perspective view of the distal end of a dual tip catheter assembly having an expandable member that is capable of inflating to a predetermined uniform expandable member inflated diameter, tapered from distal to proximal.
Figure 28:
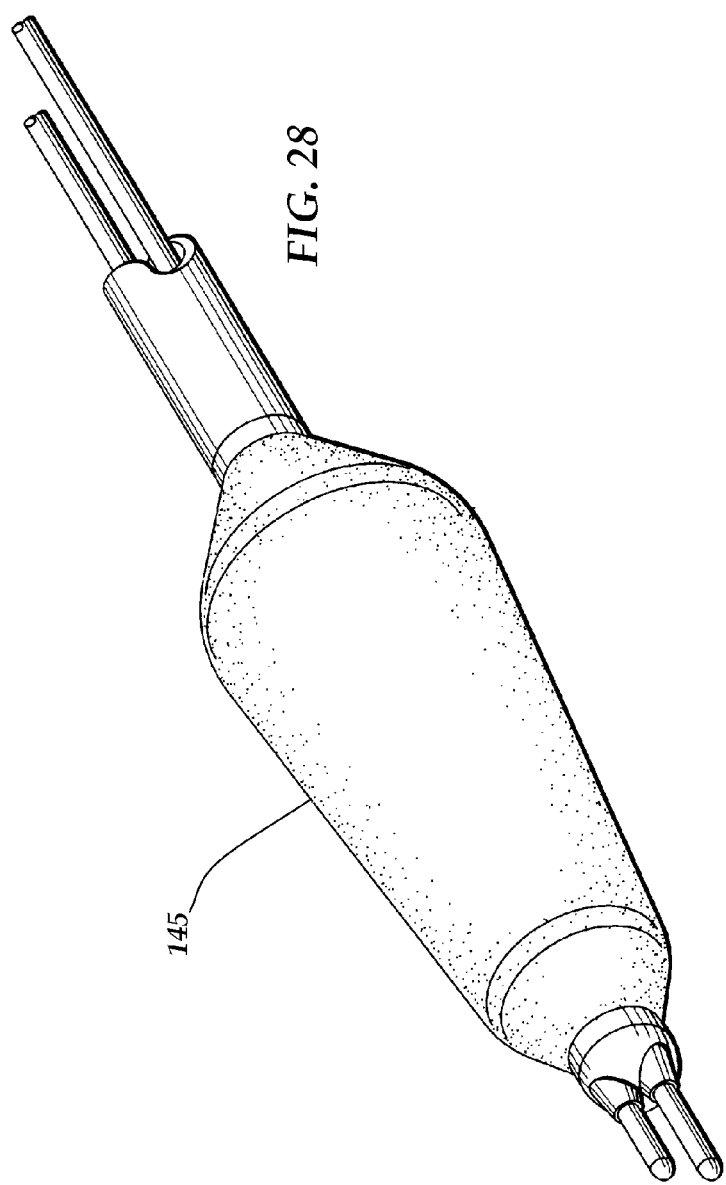
FIG. 28 is a perspective view of the distal end of a dual tip catheter assembly having an expandable member that is capable of inflating to a predetermined uniform expandable member inflated diameter, tapered from proximal to distal.

FIG. 27 is a perspective view of the distal end of a dual tip catheter assembly having an expandable member that is capable of inflating to a predetermined uniform expandable member inflated diameter 125, but is tapered from distal to proximal. The expandable member, as tapered, is identified as a proximally tapered expandable member 143. Likewise, FIG. 28 is a perspective view of the distal end of a dual tip catheter assembly having an expandable member that is capable of inflating to a predetermined uniform expandable member inflated diameter 125, as tapered from proximal to distal. The expandable member, as tapered, is identified as a distally tapered expandable member 145. The use of a distally tapered expandable member 145 is made in order to more precisely address the architecture of the single vessel, or bifurcation or trifurcation lesion. Using any of these three combinations, including the tapered expandable members, allows the physician to better respond to the positioning of wire stents 109. For example, an increase in diameter in the distal aspect of the balloon allows for an increase in opening of the bifurcation and ultimately to provide vessel shape that more closely resembles the normal branching of tubes to approximate normal laminar blood flow which is less likely to provoke regrowth of tissue than turbulent flow.

The use of the tapered expandable member is useful not only in conjunction with the multi-tipped catheter but also in connection with single tip conventional wire stent and single tip catheter assembly. Using a combination of the proximally tapered expandable member 143 and the distally tapered expandable member 145 in this process may ensure the diseased area receives proper coverage by several wire stents 109 and respects the flow characteristics surrounding a vessel bifurcation.

I claim:

1. A percutaneous procedure useful for treating vasculature lesions having plaque or occlusion comprising the steps of:
   (a) locating within a patient subject a lesion having plaque or occlusion that is affecting the blood flow of the vasculature, such lesion having a proximal main branch area, a distal main branch area, a side branch area, and a carina;
   (b) positioning into the distal main branch area a first guide wire having a distal tip and a proximal tip, until the distal tip of the first guide wire extends through the distal main branch area beyond the bifurcation lesion;
   (c) positioning into the side branch area a second guide wire having a distal tip and a proximal tip, until the distal tip of the second guide wire extends through the side branch area beyond the bifurcation lesion;
   (d) advancing simultaneously along the first guide wire and the second guide wire a plural tip catheter having a proximal end and a distal end, a proximal connector at the proximal end, a tapered expandable member at the distal end, a first guide wire lumen beginning at the distal end and extending at least a portion of the longitudinal length of the catheter, a second guide wire lumen beginning at the distal end and extending at least a portion of the longitudinal length of the catheter, and a pressurizing lumen extending substantially the entire length of the catheter;
   (e) advancing the plural tip catheter to the carina;
   (f) expanding the tapered expandable member of the plural tip catheter in the proximal main branch area to a predetermined diameter to reconfigure the plaque or occlusion;
   (g) deflating the tapered expandable member;
   (h) removing the plural tip catheter, leaving in position the first guide wire and the second guide wire;

(i) advancing along the first guide wire a single tip catheter having a proximal end and a distal end, a proximal connector at the proximal end, an expandable member at the distal end, a single guide wire lumen beginning at the distal end and extending at least a portion of the longitudinal length of the catheter, and a pressurizing lumen extending substantially the entire length of the catheter;

(j) advancing the single tip catheter to a location distal to the carina;

(k) expanding the expandable member of the single tip catheter to a predetermined diameter to reconfigure the plaque or occlusion;

(l) deflating the expandable member of the single tip catheter;

(m) removing the single tip catheter, leaving in position the first guide wire and the second guide wire;

(n) repeating the advancing of the single tip catheter along the first guide wire or the second guide wire to reconfigure the plaque or occlusion as needed; and (o) removing the first guide wire and the second guide wire at the conclusion of the procedure.

2. The percutaneous procedure of claim 1 further comprising use of an expandable wire stent associated with the tapered expandable member of the plural tip catheter.

3. The percutaneous procedure of claim 1 further comprising use of an expandable wire stent associated with the expandable member of the single tip catheter.

4. A percutaneous procedure useful for treating vasculature lesions having plaque or occlusion comprising the steps of:

(a) locating within a patient subject a lesion having plaque or occlusion that is affecting the blood flow of the vasculature, such lesion having a proximal main branch area, a distal main branch area, a side branch area, and a carina;

(b) advancing to the lesion a plural tip catheter having a proximal end and a distal end, a proximal connector at the proximal end, a tapered expandable member at the distal end, a first guide wire lumen beginning at the distal end and extending at least a portion of the longitudinal length of the catheter, a second guide wire lumen beginning at the distal end and extending at least a portion of the longitudinal length of the catheter, and a pressurizing lumen extending substantially the entire length of the catheter;

(c) extending into the distal main branch area from the plural tip catheter a first guide wire having a distal tip and a proximal tip, until the distal tip of the first guide wire extends through the distal main branch area beyond the bifurcation lesion;

(d) expanding the tapered expandable member of the plural tip catheter in the proximal main branch area to a predetermined diameter to reconfigure the plaque or occlusion;

(e) deflating the tapered expandable member;

(f) removing the plural tip catheter, leaving in position the first guide wire and the second guide wire;

(g) advancing along the first guide wire a single tip catheter having a proximal end and a distal end, a proximal connector at the proximal end, an expandable member at the distal end, a single guide wire lumen beginning at the distal end and extending at least a portion of the longitudinal length of the catheter, and a pressurizing lumen extending substantially the entire length of the catheter;

(h) advancing the single tip catheter to a location distal to the carina;

(i) expanding the expandable member of the single tip catheter to a predetermined diameter to reconfigure the plaque or occlusion;

(j) deflating the expandable member of the single tip catheter;

(k) removing the single tip catheter, leaving in position the first guide wire and the second guide wire;

(l) repeating the advancing of the single tip catheter along the first guide wire or the second guide wire to reconfigure the plaque or occlusion as needed; and (m) removing the first guide wire and the second guide wire at the conclusion of the procedure.

* * * * *